(12) United States Patent
Morita

(10) Patent No.: US 8,340,380 B2
(45) Date of Patent: Dec. 25, 2012

(54) MAMMARY GLAND CONTENT RATE ESTIMATING APPARATUS, METHOD AND RECORDING MEDIUM

(75) Inventor: Junya Morita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 448 days.

(21) Appl. No.: 12/751,363

(22) Filed: Mar. 31, 2010

(65) Prior Publication Data

US 2010/0246924 A1 Sep. 30, 2010

(30) Foreign Application Priority Data

Mar. 31, 2009 (JP) .................................. 2009-087493
Jan. 20, 2010 (JP) .................................. 2010-010239

(51) Int. Cl.
*G06K 9/00* (2006.01)
(52) U.S. Cl. ...................................... 382/128
(58) Field of Classification Search .................. 382/128, 382/131, 132; 250/363.04; 378/4, 21, 37
See application file for complete search history.

(56) References Cited

U.S. PATENT DOCUMENTS

| | | | | |
|---|---|---|---|---|
| 6,556,655 | B1 * | 4/2003 | Chichereau et al. | 378/108 |
| 8,160,346 | B2 * | 4/2012 | Gatesoupe et al. | 382/132 |
| 2004/0125999 | A1 * | 7/2004 | Iordache et al. | 382/132 |
| 2006/0094950 | A1 * | 5/2006 | Ning | 600/407 |
| 2008/0075228 | A1 * | 3/2008 | Tasaki | 378/37 |
| 2008/0187095 | A1 * | 8/2008 | Boone et al. | 378/37 |
| 2009/0086891 | A1 | 4/2009 | Ofuji | |
| 2009/0087045 | A1 * | 4/2009 | Partain et al. | 382/128 |

FOREIGN PATENT DOCUMENTS

| | | | |
|---|---|---|---|
| JP | 2002-125961 A | 5/2002 | |
| JP | 2005-065855 A | 3/2005 | |

OTHER PUBLICATIONS

EP Communication, dated Jul. 21, 2010, issued in corresponding EP Application No. 10157974.6, 6 pages.
Roller et al., "A Method for Interpreting Pixel Grey Levels in Digital Mammography," Image Analysis and Recognition Lecture Notes in Computer Science, Jan. 1, 2006, pp. 580-588, XP019043817.
Kappadath et al., "Dual-energy digital mammography: Calibration and inverse-mapping techniques to estimate calcification thickness and glandular-tissue ratio," Medical Physics, vol. 30, No. 6, Jun. 1, 2003, pp. 1110-1117, XP012012104.

(Continued)

*Primary Examiner* — Wesley Tucker
*Assistant Examiner* — Shervin Nakhjavan
(74) *Attorney, Agent, or Firm* — Sughrue Mion, PLLC

(57) ABSTRACT

A mammary gland content rate estimating apparatus, includes: a breast image acquiring device which acquires a breast image obtained by radiographing a breast by a mammography imaging apparatus; an adipose image estimating device which estimates an adipose image from the acquired breast image based on an assumption that an entire breast is composed of only adipose tissues; a device which acquires a pixel value of a directly irradiated region from the acquired breast image; and a mammary gland content rate calculating device which calculates a mammary gland content rate for each of pixels in the breast image based on the acquired breast image, the estimated adipose image and the acquired pixel value of the directly irradiated region. Accordingly, without requiring complicated calibration in advance, the mammary gland content rate can be estimated for each of pixels easily and precisely.

13 Claims, 17 Drawing Sheets

OTHER PUBLICATIONS

T. Amano, et al., "Measurement of Glandular Dose Using Digital Mammogram," Medical Imaging and Information Sciences, 2007, pp. 6-12, vol. 24, No. 1.

P. Snoeren, et al., "Thickness Correction of Mammographic Images by Anisotropic Filtering and Interpolation of Dense Tissue," Proc. SPIE (Medical Imaging Image Processing), 2005, pp. 1521-1527, vol. 5747.

S. van Engeland, et al., "Volumetric Breast Density Estimation From Full-Field Digital Mammograms," IEEE Transactions of Medical Imaging, Mar. 2006, pp. 273-282, vol. 25, No. 3.

* cited by examiner

| | μa | μg | μg−μa | μg/μa |
|---|---|---|---|---|
| Mo/Mo | 0.568 | 1.049 | 0.481 | 1.846 |
| Mo/Rh | 0.529 | 0.962 | 0.433 | 1.820 |
| W/Rh | 0.475 | 0.843 | 0.368 | 1.776 |

4cm

| | μa | μg | μg−μa | μg/μa |
|---|---|---|---|---|
| Mo/Mo | 0.511 | 0.924 | 0.413 | 1.807 |
| Mo/Rh | 0.477 | 0.849 | 0.372 | 1.779 |
| W/Rh | 0.438 | 0.763 | 0.325 | 1.741 |

8cm

| | μa | μg | μg−μa | μg/μa |
|---|---|---|---|---|
| Mo/Mo | 0.430 | 0.744 | 0.314 | 1.732 |
| Mo/Rh | 0.417 | 0.716 | 0.299 | 1.717 |
| W/Rh | 0.404 | 0.687 | 0.283 | 1.701 |

⊞ : MAMMARY GLAND
    REGION

▨ : ADIPOSE REGION

▩ : GREATER PECTORAL
    MUSCLE REGION

☐ : NON-RADIOGRAPHY
    REGION
    (NON-BREAST REGION)

⊞ : MAMMARY GLAND
    REGION

▨ : ADIPOSE REGION

▩ : GREATER PECTORAL
    MUSCLE REGION

☐ : NON-RADIOGRAPHY
    REGION
    (NON-BREAST REGION)

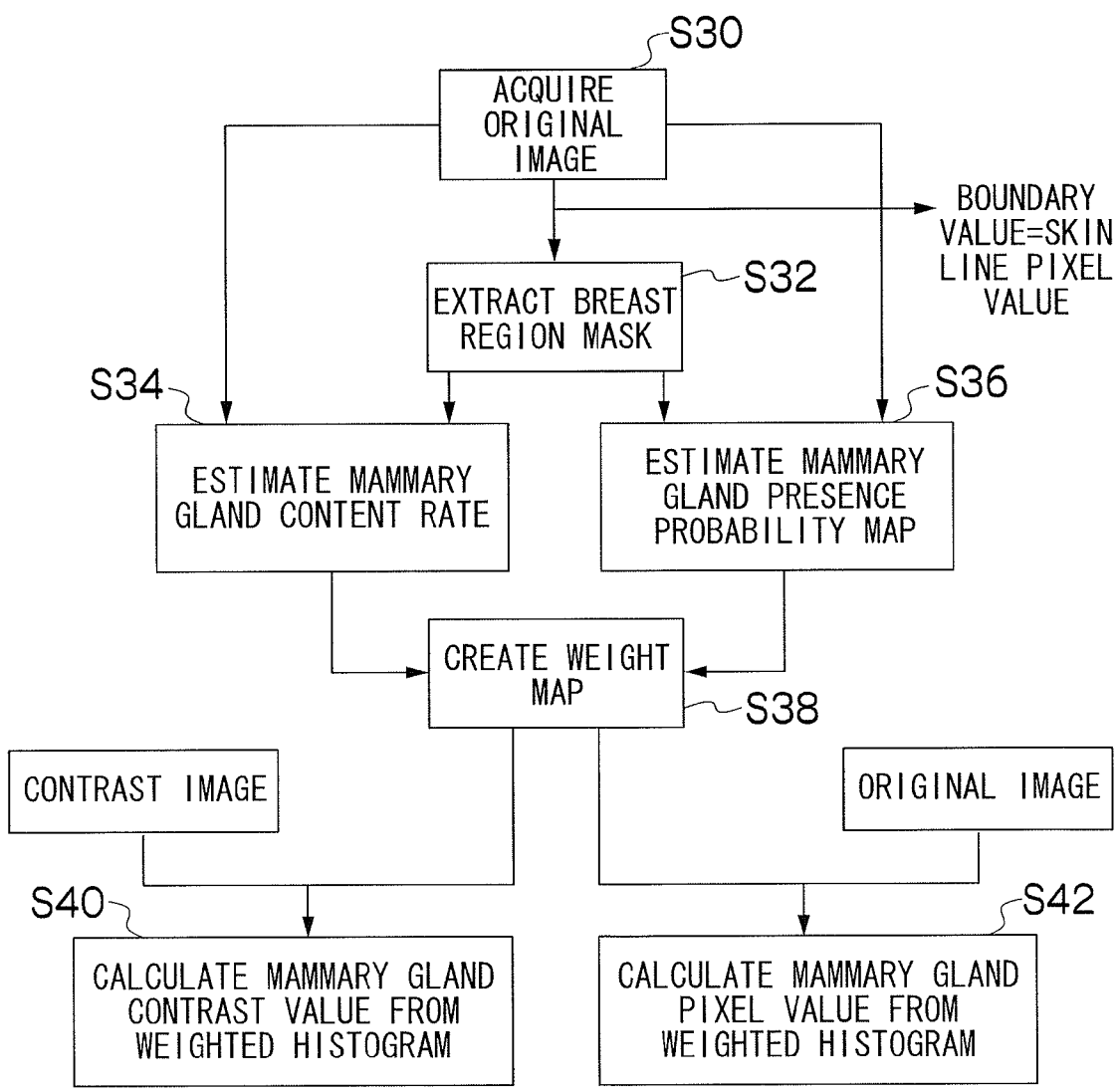

ORIGINAL IMAGE

BREAST REGION MASK

MAMMARY GLAND CONTENT RATE ESTIMATION

MAMMARY GLAND PRESENCE PROBABILITY MAP ESTIMATION

WEIGHT MAP

CONTRAST IMAGE (SAME AS FIG.14A)
ORIGINAL IMAGE

POINT C
POINT A
POINT B

MAMMARY GLAND PRESENCE PROBABILITY MAP

MAMMARY GLAND CONTENT RATE ESTIMATING APPARATUS, METHOD AND RECORDING MEDIUM

CROSS-REFERENCE TO RELATED APPLICATIONS

This application claims the priority benefit under 35 U.S.C. §119 of Japanese Patent Application No. 2009-087493 filed on Mar. 31, 2009 and Japanese Patent Application No. 2010-010239 filed on Jan. 20, 2010, which are hereby incorporated in their entirety by reference.

BACKGROUND OF THE INVENTION

1. Field of the Invention

The presently disclosed subject matter relates to an apparatus and a method for estimating mammary gland content rate, particularly, to technology for estimating a mammary gland content rate for each pixel in a breast image from only the breast image obtained by radiographing a breast by a mammography imaging apparatus.

2. Description of the Related Art

A breast is mainly constituted of mammary gland tissue and adipose tissue, and the ratio of the mammary glands in the breast is called a mammary gland content rate. The mammary gland content rate is extremely useful in accurately knowing the character of a breast, and is medically indispensable information. For example, a study suggests that a correlation exists between the mammary gland content rate and the risk of cancer.

At present, classification and evaluation of the composition of a breast (the degree of mammary gland involution is classified into four stages of adipose, scattered mammary gland, nonuniform high density, and high density) are performed qualitatively based on the contrast difference of mammary gland and adipose by vision, but the evaluations are likely to be inconsistent depending on radiogram interpreters, and more quantitative evaluation is required.

Conventionally, as the method for quantitatively evaluating a mammary gland content rate, there is the method disclosed in Japanese Patent Application Laid-Open No. 2002-125961. In this method, mammary glands are classified, for example, with the density of the pectoral muscle as the reference, the variation of the mammary gland region is converted into histogram, and what is the mammary gland ratio in the breast is determined (paragraph [0029] of Japanese Patent Application Laid-Open No. 2002-125961).

Meanwhile, there is proposed the method for estimating a mammary gland content rate for each of pixels in a breast image. By calculating the mammary gland content rate for each of the pixels, application to various applications is enabled (aid of diagnosis, CAD (Computer-Aided Detection), image processing condition setting, and QA). In "Measurement of Glandular Dose Using Digital Mammogram", Medical Imaging and Information Sciences, Vol. 24, No. 1, pp. 6-12, 2007, the mammary gland content rate is calculated for each of pixels based on the dose ratio (transit dose/exposure dose), breast mass thickness, and the relationship between a pixel value and a mammary gland content rate (previously obtained relational expression).

Further, "Volumetric Breast Density Estimation From Full-Field Digital Mammograms", IEEE Trans. MEDICAL IMAGING, Vol. 25, No. 3, 2006 discloses the technology for calculating the attenuation coefficients of mammary gland and adipose based on the information of the X-ray tube voltage obtained from the imaging apparatus, the target/filter and the breast mass thickness, and estimating the volume of the mammary glands based on the isopachic correction image estimated by "Thickness correction of mammographic images by anisotropic filtering and interpolation of dense tissue", Proc. SPIE (Medical Imaging: Image Processing), Vol. 5747, pp. 1521-1527, 2005, and the respective attenuation coefficients.

SUMMARY OF THE INVENTION

In the method disclosed in Japanese Patent Application Laid-Open No. 2002-125961, a mammary gland region is extracted from the breast image based on the densities of the pixels, and the area ratio of the mammary gland region relative to the breast region is estimated as a mammary gland content rate. However, since a breast is composed of mammary glands and adipose which are mixed up together, there is the problem that the mammary gland region cannot be clearly separated from the adipose region in the two-dimensional image. Further, there is also the problem that the area ratio changes depending on the way of compressing a breast and positioning at the time of imaging.

Meanwhile, in the method disclosed in "Measurement of Glandular Dose Using Digital Mammogram", Medical Imaging and Information Sciences, Vol. 24, No. 1, pp. 6-12, 2007, the relational expressions of the dose ratio, the breast mass thickness, the pixel value and the mammary gland content rate need to be obtained in advance for each mammography imaging apparatus, and complicated calibration is required in advance. Further, in order to select suitable relational expressions, the information of the breast mass thickness and the like is required, and a mammary gland content rate cannot be estimated with only the image data of the breast image.

Further, in the method disclosed in "Volumetric Breast Density Estimation From Full-Field Digital Mammograms", IEEE Trans. MEDICAL IMAGING, Vol. 25, No. 3, 2006, the volume of mammary glands and the volume ratio can be calculated, but a mammary gland content rate cannot be calculated for each of pixels. Further, the imaging information relating to imaging such as the X-ray tube voltage and the target/filter at the time of radiographing, and breast mass thickness needs to be acquired, and there arises the problem that the volume of mammary glands and the volume ratio cannot be estimated when the imaging information cannot be acquired.

The presently disclosed subject matter is made in view of the above circumstances, and has an object to provide an apparatus and method for estimating mammary gland content rate, which can estimate a mammary gland content rate for each of pixels easily and precisely without requiring complicated calibration in advance.

In order to attain the above-described object, a mammary gland content rate estimating apparatus according to a first aspect of the presently disclosed subject matter, includes: a breast image acquiring device which acquires a breast image obtained by radiographing a breast by a mammography imaging apparatus; an adipose image estimating device which estimates an adipose image from the acquired breast image based on an assumption that an entire breast is composed of only adipose tissues; a device which acquires a pixel value of a directly irradiated region from the acquired breast image; and a mammary gland content rate calculating device which calculates a mammary gland content rate for each of pixels in the breast image based on the acquired breast image, the estimated adipose image and the acquired pixel value of the directly irradiated region.

In the first aspect of the invention, the adipose image (image having pixel values in the case where the mammary gland tissue of the breast is all replaced with the adipose tissue) is estimated from the X-ray image of the breast (breast image), and the mammary gland content rate is calculated for each of the pixels based on the relationship between the original breast image and the adipose image. At the time of calculation of the mammary gland content rate, the pixel value of the directly irradiated region (region without X-ray attenuation) in the breast image is used in addition to the breast image and the adipose image. By using the adipose image and the pixel value of the directly irradiated region which are obtained by analyzing the breast image, and the relational expressions between them, the mammary gland content rate can be estimated easily with high precision for each of pixels, without requiring complicated calibration in advance.

According to a second aspect of the presently disclosed subject matter, the mammary gland content rate estimating apparatus according to the first aspect of the invention, further includes a storage device which stores a predetermined value indicating a ratio of average attenuation coefficients of mammary glands and adipose, wherein the mammary gland content rate calculating device calculates the mammary gland content rate for each of the pixels in the breast image based on the acquired breast image, the estimated adipose image, the acquired pixel value of the directly irradiated region, and further, the stored predetermined value indicating the ratio of the average attenuation coefficients.

Here, the average attenuation coefficients of the mammary gland and adipose are values which significantly change in accordance with the imaging conditions (X-ray tube voltage, kinds of target/filter, breast mass thickness), and in order to avoid the influence of them, in "Volumetric Breast Density Estimation From Full-Field Digital Mammograms", IEEE Trans. MEDICAL IMAGING, Vol. 25, No. 3, 2006, the values corresponding to the imaging conditions are read from the attenuation coefficient table set in advance. However, according to the study by the present inventor, it is newly found out that the value of the ratio of the average attenuation coefficients is the value which is hardly influenced by the imaging conditions. By calculating the mammary gland content rate using the predetermined value of the average attenuation coefficient ratio, the mammary gland content rate can be estimated from only the image data with high precision without acquiring the information concerning imaging.

According to a third aspect of the presently disclosed subject matter, in the mammary gland content rate estimating apparatus according to the second aspect of the invention, the mammary gland content rate calculating device calculates a mammary gland content rate $G(x, y)$ of each of pixels in coordinates $(x, y)$ of the breast image by the following expression:

$$G(x, y) = \frac{A(x, y) - I(x, y)}{I_0 - A(x, y)} \times \frac{1}{\mu - 1} \qquad [\text{Expression 1}]$$

where a pixel value in the coordinates $(x, y)$ in the acquired breast image is set as $I(x, y)$, a pixel value in coordinates $(x, y)$ of the estimated adipose image is set as $A(x, y)$, the acquired pixel value of the directly irradiated region is set as $I_0$, and the stored predetermined value expressing the ratio of the average attenuation coefficients is set as $\mu$.

As shown in [Expression 1], information concerning imaging is not included in the expression, and the mammary gland content rate $G(x, y)$ of each of the pixels of the respective coordinates $(x, y)$ of the breast image can be calculated from the pixel value $I(x, y)$ in the coordinates $(x, y)$ of the original breast image, the pixel value $A(x, y)$ in the coordinates $(x, y)$ of the adipose image, the pixel value $I_0$ of the directly irradiated region which are obtained from the original breast image, and the predetermined value $\mu$ which indicates the ratio of the average attenuation coefficients (values which are hardly influenced by the imaging conditions).

According to a fourth aspect of the presently disclosed subject matter, the mammary gland content rate estimating apparatus according to the third aspect of the invention, the mammary gland content rate estimating apparatus is characterized by further includes a mammary gland volume ratio calculating device which calculates a volume ratio of the mammary glands by calculating a weighted average of the mammary gland content rates $G(x, y)$ using $(I_0 - A(x, y))$ of [Expression 1] as a weight.

It is difficult to obtain the volume of the entire breast and the volume of the mammary glands, but from the mammary gland content rate of each of the pixels in the breast image obtained from the [Expression 1], the mammary gland volume ratio can be estimated.

According to a fifth aspect of the presently disclosed subject matter, in the mammary gland content rate estimating apparatus according to any one of the first to the fourth aspects, the predetermined value indicating the ratio of the average attenuation coefficients of the mammary glands and the adipose is a fixed value which indicates a ratio of an average attenuation coefficient of mammary glands and an average attenuation coefficient of adipose when an average breast is imaged under average imaging conditions by the mammography imaging apparatus.

The predetermined value indicating the ratio of the average attenuation coefficients is the value which is hardly influenced by the imaging conditions, but is not completely free from influence. Thus, as the predetermined value indicating the ratio of the average attenuation coefficients, the value (fixed value) indicating the ratio of the average attenuation coefficient of the mammary glands and the average attenuation coefficient of the adipose in the case of imaging the average breast under the average conditions is adopted, and thereby, the error in estimation of the mammary gland content rate can be minimized.

According to a sixth aspect of the presently disclosed subject matter, in the mammary gland content rate estimating apparatus according to any one of the first to the fifth aspects, the predetermined value indicating the ratio of the average attenuation coefficients of the mammary glands and the adipose is about 1.778.

According to a seventh aspect of the presently disclosed subject matter, in the mammary gland content rate estimating apparatus according to any one of the first to the sixth aspects, the adipose image estimating device includes: a skin line extracting device which extracts a skin line showing a boundary between a breast region and the directly irradiated region based on the acquired breast image; and an adipose image creating device which creates the adipose image by setting a pixel value of a pixel at an equal distance from the skin line at a pixel value determined in accordance with the distance from the skin line, based on an assumption that a thickness of a breast which is imaged is determined in accordance with a distance in a normal direction from the skin line.

When the entire breast is assumed to be composed of only the adipose tissue, the adipose image has different pixel values in accordance with the breast mass thickness at the time of imaging. Thus, it is assumed that the thickness of the breast which is imaged is determined in accordance with the distance in the normal direction from the skin line, and the adipose image is created by setting the pixel values of a pixel at the equal distance from the skin line at the pixel value determined in correspondence with the distance from the skin line.

According to an eighth aspect of the presently disclosed subject matter, in the mammary gland content rate estimating apparatus according to the seventh aspect, the adipose image creating device includes: a device which calculates a representative value representing adipose tissue from the pixel value of the pixel at the equal distance from the skin line based on the acquired breast image, for respective distances from the skin line; and a device which estimates a relational expression between the distance from the skin line and the pixel value of the adipose image based on the calculated representative value, wherein the pixel value of the adipose image corresponding to the distance from the skin line is determined based on the estimated relational expression.

The adipose image creating device calculates the representative value representing the adipose tissue from the pixel value of each of the pixels at the equal distance from the skin line based on the acquired breast image. As the representative value, the median value, the average value, the mode value, the extremal value and the like of a plurality of pixel values are conceivable. As described above, the representative value is calculated for each of different distances from the skin line, and then, based on the representative values, the relational expression between the distance from the skin line and the pixel value of the adipose image is estimated. For example, the coefficient of the curve approximation expression showing the relational expression is determined by substituting the representative value into the approximation expression.

A mammary gland content rate estimating method according to a ninth aspect of the presently disclosed subject matter, includes the steps of: acquiring a breast image obtained by radiographing a breast by a mammography imaging apparatus; estimating an adipose image from the acquired breast image based on an assumption that an entire breast is composed of only adipose tissues; acquiring a pixel value of a directly irradiated region from the acquired breast image; and calculating a mammary gland content rate for each of pixels of the breast image based on the acquired breast image, the estimated adipose image and the acquired pixel value of the directly irradiated region.

According to a tenth aspect of the presently disclosed subject matter, the mammary gland content rate estimating method according to the ninth aspect of the invention further includes the step of: storing, in a storage device, a predetermined value indicating a ratio of average attenuation coefficients of mammary glands and adipose, in advance, wherein in the step of calculating the mammary gland content rate, the mammary gland content rate is calculated for each of the pixels in the breast image based on the acquired breast image, the estimated adipose image, the acquired pixel value of the directly irradiated region, and further, the predetermined value indicating the ratio of the average attenuation coefficients.

According to an eleventh aspect of the presently disclosed subject matter, in the mammary gland content rate estimating method according to the tenth aspect of the invention, in the step of calculating a mammary gland content rate, a mammary gland content rate $G(x, y)$ of each of pixels in coordinates $(x, y)$ of the breast image is calculated by the following expression:

$$G(x, y) = \frac{A(x, y) - I(x, y)}{I_0 - A(x, y)} \times \frac{1}{\mu - 1} \quad \text{[Expression 2]}$$

where a pixel value in the coordinates $(x, y)$ in the acquired breast image is set as $I(x, y)$, a pixel value in coordinates $(x, y)$ of the estimated adipose image is set as $A(x, y)$, the acquired pixel value of the directly irradiated region is set as $I_0$, and the stored predetermined value expressing the ratio of the average attenuation coefficients is set as $\mu$.

According to a twelfth aspect, the mammary gland content rate estimating method according to the eleventh aspect of the invention, further includes the step of calculating a weighted average of the mammary gland content rates $G(x, y)$ using $(I_0 - A(x, y))$ of [Expression 1] as a weight to obtain a volume ratio of the mammary glands.

According to a thirteenth aspect, a recording medium on which a program is recorded, the program comprising computer-executable instructions of: acquiring a breast image obtained by radiographing a breast by a mammography imaging apparatus; estimating an adipose image from the acquired breast image based on an assumption that an entire breast is composed of only adipose tissues; acquiring a pixel value of a directly irradiated region from the acquired breast image; and calculating a mammary gland content rate for each of pixels of the breast image based on the acquired breast image, the estimated adipose image and the acquired pixel value of the directly irradiated region.

According to the presently disclosed subject matter, the adipose image (the image having the pixel value in the case where the mammary gland tissue of the breast is all replaced with the adipose tissue) is estimated from the X-ray image (breast image) of the breast, the pixel value of the directly irradiated region without X-ray attenuation is analyzed, and the mammary gland content rate is calculated based on the relationship between the original breast image, the adipose image and the pixel value of the directly irradiated region. Therefore, the mammary gland content rate can be estimated for each of pixels easily and precisely, without requiring complicated calibration in advance.

BRIEF DESCRIPTION OF THE DRAWINGS

FIG. 7 is a table showing calculation results of an average attenuation coefficient $\bar{\mu}_g$ of mammary gland, an average attenuation coefficient $\bar{\mu}_a$ of adipose, a difference of these average attenuation coefficients, and a ratio in each of a plurality of imaging conditions;

FIG. 13 is a flowchart showing a flow of image analysis processing;

DETAILED DESCRIPTION OF THE PREFERRED EMBODIMENTS

Hereinafter, a preferred embodiment of an apparatus and method for estimating mammary gland content rate (mammary gland content rate estimating apparatus and method) according to the presently disclosed subject matter will be described in accordance with the attached drawings.

[Apparatus Configuration]

Figure 1:
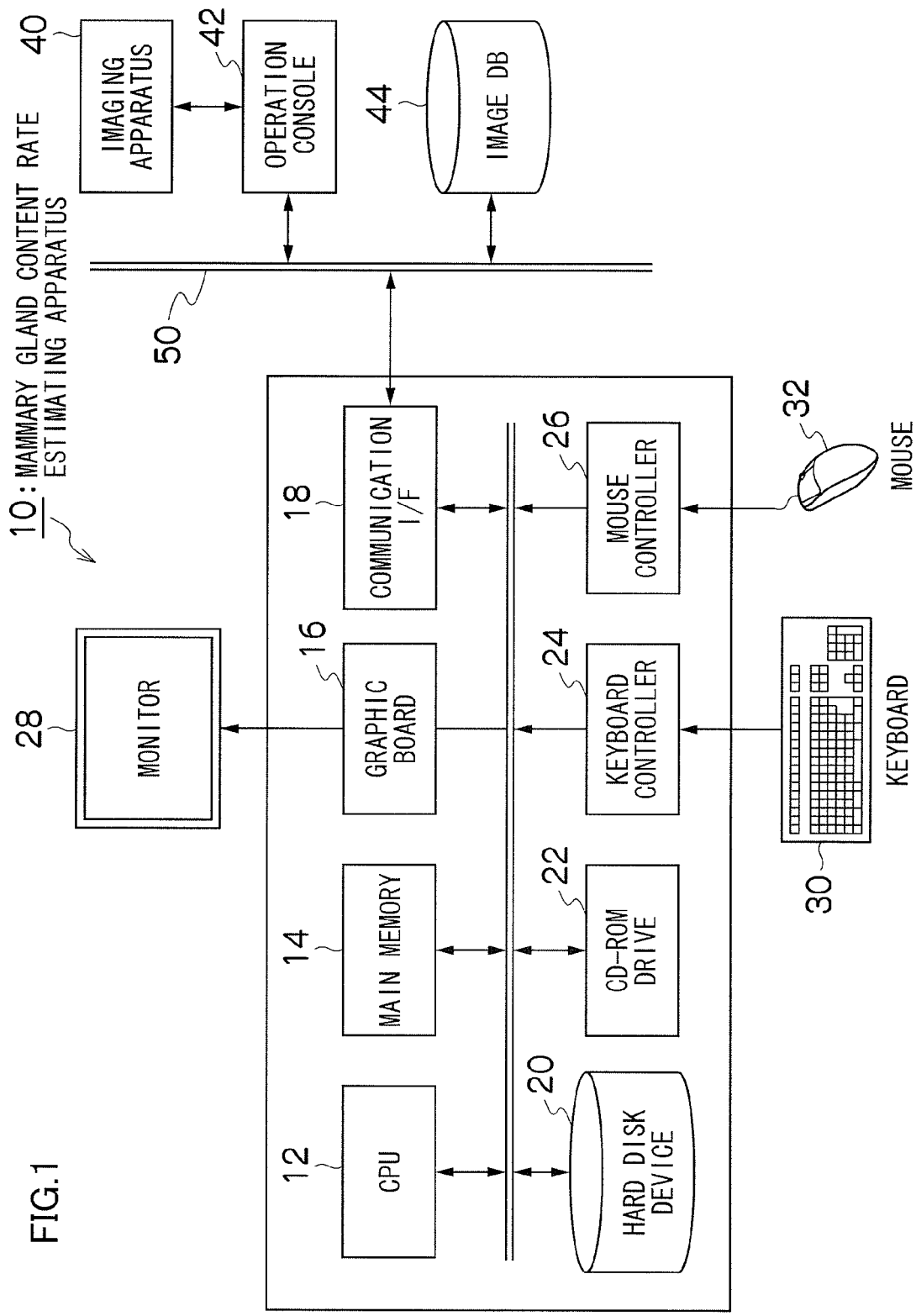
FIG. 1 is a system configuration diagram including an apparatus for estimating mammary gland content rate according to an embodiment of the presently disclosed subject matter.

FIG. 1 is a system configuration diagram including the mammary gland content rate estimating apparatus according to the presently disclosed subject matter.

The system includes a mammary gland content rate estimating apparatus 10 according to an embodiment of the presently disclosed subject matter, a mammography imaging apparatus 40 placed in a medical facility or the like, an operation console 42 for performing an operation or the like of the mammography imaging apparatus 40, an image database (image DB) 44 which stores mammary images which are taken by the mammography imaging apparatus 40.

The mammary gland content rate estimating apparatus 10 is configured by a computer such as a work station, and mainly includes a central processing unit (CPU) 12 which controls the operation of each of components, a main memory 14 which stores a control program of the apparatus and becomes a working area at the time of execution of the program, a graphic board 16 which controls display of a monitor device 28 such as a liquid crystal display, or a CRT (Cathode Ray Tube) display, a communication interface (communication I/F) 18 which is connected to a network 50 of a medical facility, a hard disk device 20 which stores various kinds of application software including a program for estimation processing of mammary gland content rate according to the embodiment and an image analyzing program, a predetermined value μ showing a ratio of an average attenuation coefficient which will be described later and the like, a CD-ROM drive 22, a keyboard controller 24 which detects a key operation of a keyboard 30 and outputs it to the CPU 12 as an instruction input, and a mouse controller 26 which detects the state of a mouse 32 as a position input device and outputs signals of a position of a mouse pointer on the monitor device 28, a state of the mouse 32 and the like to the CPU 12.

<Mammography Imaging Apparatus>

Figure 2:
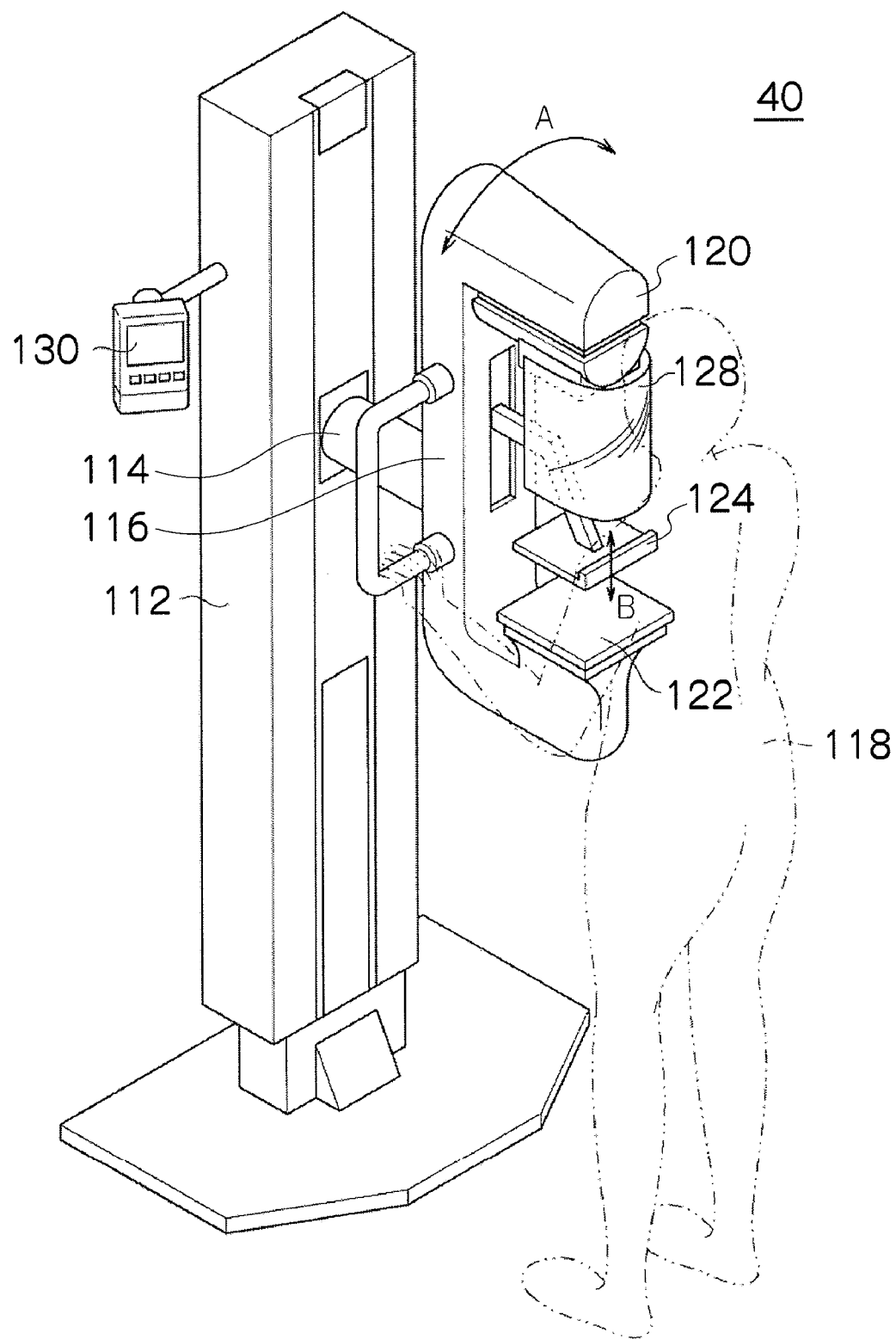
FIG. 2 is a configuration diagram showing an embodiment of a mammography imaging apparatus.

FIG. 2 is a configuration diagram showing an example of the mammography imaging apparatus 40 according to the embodiment.

The mammography imaging apparatus 40 includes a base stand placed in a raised state, an arm member 116 fixed to a turn shaft 114 placed at a substantially central portion of the base stand 112, an X-ray source housing section 120 which houses an X-ray source for exposing radiation (X-ray) to a breast of a subject 118 and is fixed to one end portion of the arm member 116, an imaging table 122 which houses a detector for detecting an X-ray transmitted through the breast to acquire X-ray image information and is fixed to the other end portion of the arm member 116, and a compression plate 124 which compresses a breast against the imaging table 122.

The arm member 116 to which the X-ray source housing section 120, the imaging table 122 and the compression plate 124 are connected is configured to turn in the direction of the arrow A with the turn shaft 114 as a center to make the imaging direction to the breast of the subject 188 adjustable. The compression plate 124 is placed between the X-ray source housing section 120 and the imaging table 122, in the state in which the compression plate 124 is connected to the arm member 116, and is configured to be movable in the direction of the arrow B.

In the X-ray source housing section 120, a face guard sheet 128 formed by a member which shuts off the X-rays is placed in order to protect an area in the vicinity of the face of the subject 118 from exposure of X-rays. At the base stand 112, a display device 130 is placed, which displays imaging information of an imaged region of the subject 118, an imaging direction and the like, ID information of the subject 118 and the like, and displays information concerning the residual compression time until the compression state of a breast by the compression plate 124 is released, in accordance with necessity.

Figure 3:
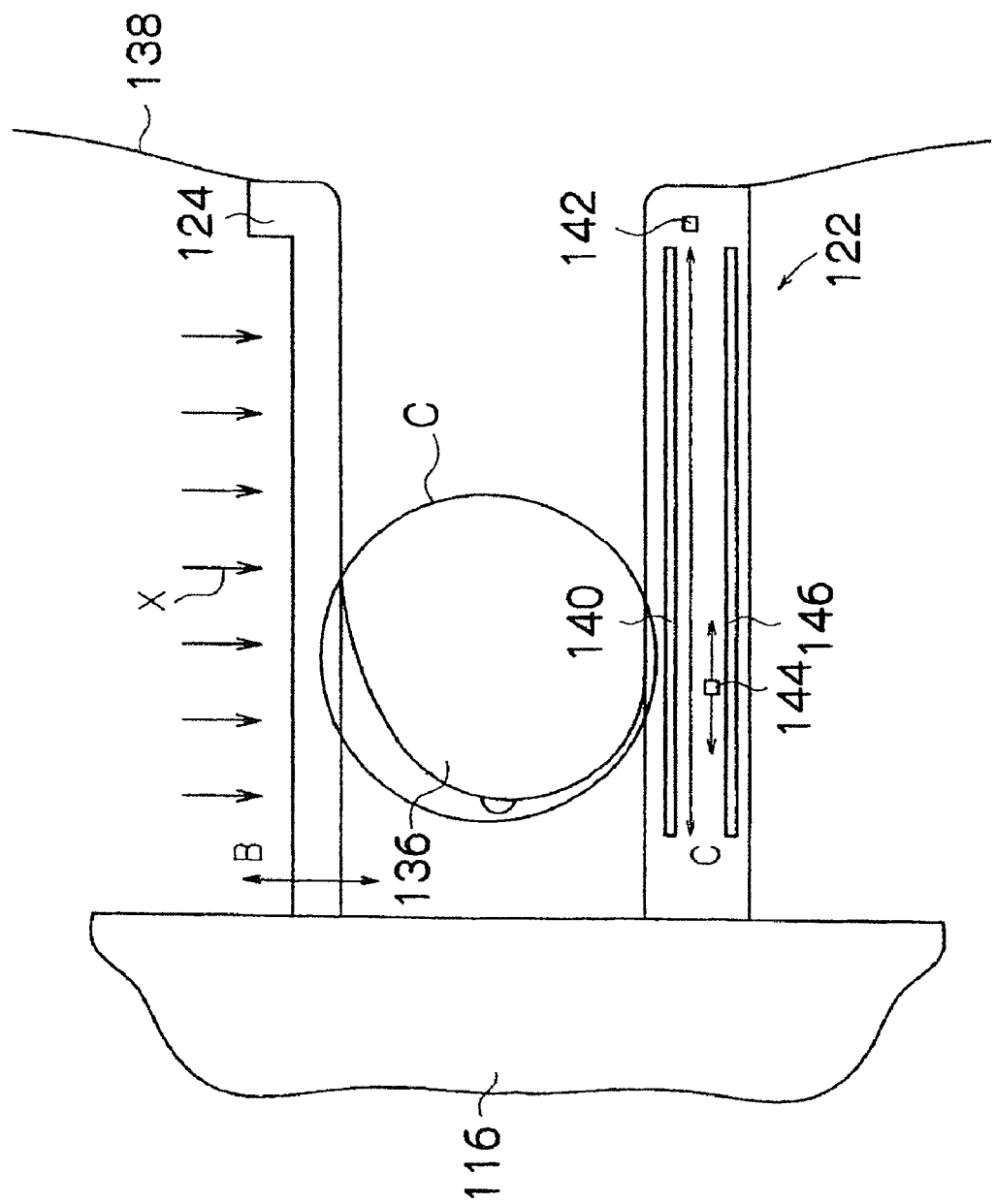
FIG. 3 is an internal configuration diagram of an imaging table in the mammography imaging apparatus.

FIG. 3 is an internal configuration diagram of the imaging table 122 in the mammography imaging apparatus 40, and shows the state in which a breast 136, which is an imaged region of the subject 118, is disposed between the imaging table 122 and the compression plate 124. Reference numeral 138 designates a chest wall of the subject 118.

The imaging table 122 is internally equipped with a detector 140 which accumulates X-ray image information based on the X-rays transmitted through the breast 136 and outputs it as an electric signal, a reading light source section 142 which irradiates reading light to the detector 140 in order to read the X-ray image information accumulated and recorded in the detector 140, a dose detector (automatic exposure controlling X-ray detector, hereinafter called "AEC (Automatic Exposure Control) sensor 144".) which detects the dose of the X-rays transmitted through the breast 136 in order to determine exposure time which is one of the X-ray exposure conditions, and an erase light source section 146 which irradiates erase light to the detector 140 in order to remove unnecessary electric charges accumulated in the detector 140.

The detector 140 is an X-ray detector of a direct conversion type and a light read type, accumulates x-ray image information based on the X-rays transmitted through the breast 136 as an electrostatic latent image, and generates a current corresponding to the electrostatic latent image by being scanned by the reading light from the reading light source section 142.

The reading light source section 142 has a line light source configured by arranging, for example, a plurality of LED chips in a row, and an optical system linearly emits the reading light outputted from the line light source onto the detector 140. The reading light source section 142 exposes and scans the entire surface of the detector 140 by moving the line light source with the LED chips arranged in the direction orthogonal to an extending direction of a linear electrode which is a second conducive layer of the detector 140, in the extending direction (direction of arrow C) of the aforementioned linear electrode.

The AEC sensor 144 is configured to be movable in the direction of the arrow C along the detector 140 so as to be able to detect an X-ray dose by being moved to the region corresponding to the portion having high mammary gland density of the breast 136, for example. The erase light source section 146 can be configured by two-dimensionally arranging LED chips which emit light/quench light in a short time and have extremely small afterglow.

The X-rays transmitted through the breast 136 are detected as the X-ray image information by the detector 140, and the X-ray image of the breast 136 is formed by an X-ray image forming section (not illustrated). Meanwhile, the detector 140 from which the X-ray image information is read is irradiated with the erase light from the erase light source section 146, and thereby, erase processing of the remaining X-ray image information is performed.

Now, when mammography imaging of the subject 118 is performed, the subject 118 performs positioning, and imaging is performed by operating the operation console 42 (FIG. 1). Further, the operation console 42 is equipped with an input device which receives subject identification information for identifying the subject (subject ID), and an radiographer ID for identifying a radiographer. The subject ID and the radiographer ID which are inputted through the operation console 42, and the breast image taken by the mammography imaging apparatus 40 are stored in the image DB 44 with being related to one another.

The breast image can be stored in the image DB 44 as, for example, an image file (DICOM file) according to the DICOM (Digital Image and Communication in Medicine) standard. In this case, information of an imaging date, an imaging facility and the like is recorded in the header of the DICOM file in addition to the aforementioned subject ID and the radiographer ID.

The detector 140 is not especially limited, and may be an imaging plate (accumulative phosphor sheet) IP having an accumulative phosphor, or a flat panel type X-ray detector (flat panel detector) FPD in which an extremely large number of X-ray detecting elements using semiconductors or the like are two-dimensionally arranged on an X-ray detection surface.

[Principle of Mammary Gland Content Estimation]

Next, the principle of the mammary gland content rate estimating method according to the presently disclosed subject matter will be described.

Figure 4:
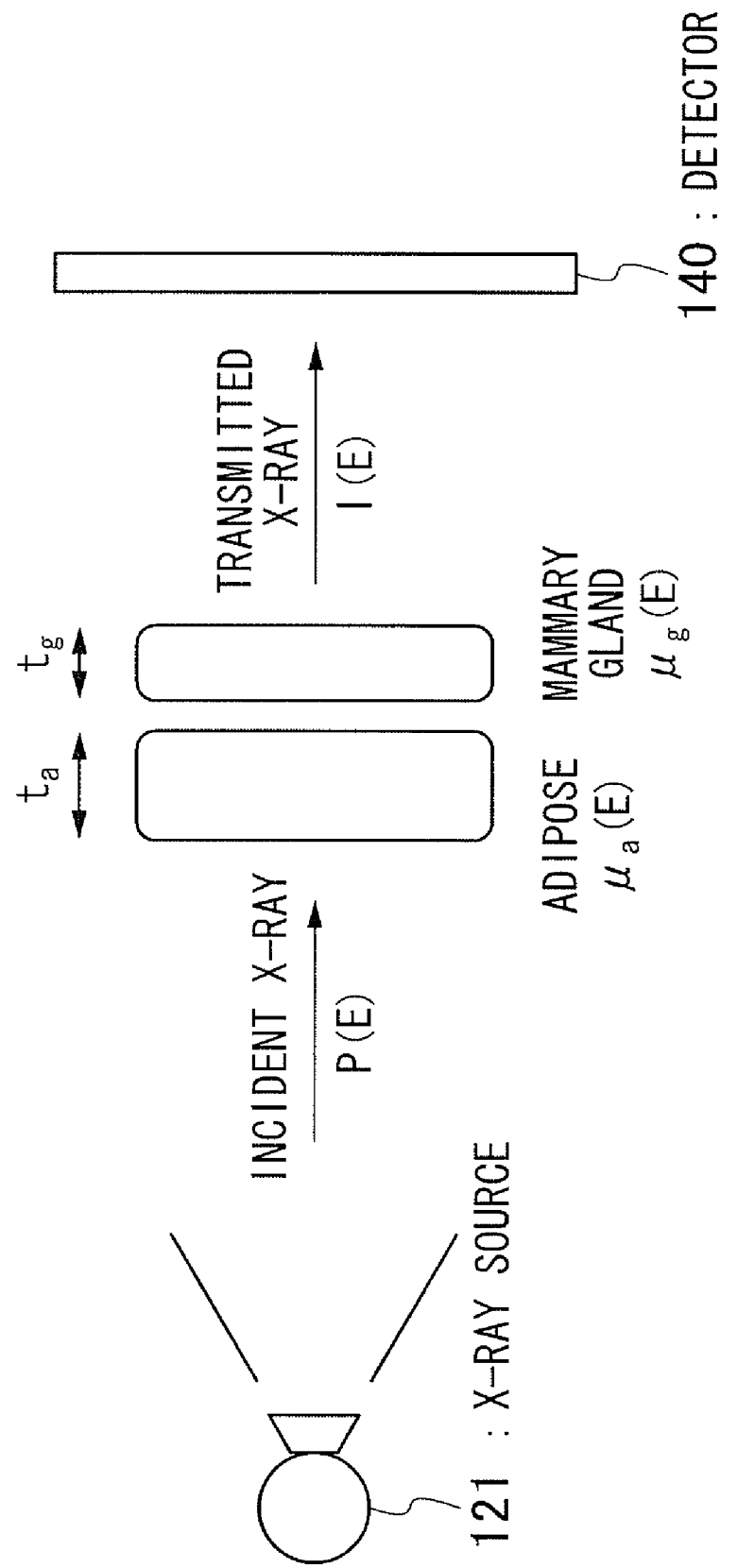
FIG. 4 is a schematic diagram showing the relationship of an X-ray source, an imaged object (breast) and a detector at a time of mammography imaging.

FIG. 4 is a schematic diagram showing the relationship between the X-ray source, an imaged object (breast) and the detector, at the time of mammography imaging.

As shown in FIG. 4, an X-ray P(E) irradiated from an X-ray source 121 passes through adipose having a thickness of $t_a$ and mammary gland having a thickness of $t_g$. The transmitted X-ray I(E) passed through them is detected by the detector 140.

An X-ray dose (integration of X-ray distribution) I which reaches the detector 140 can be expressed by the following expression.

$$I = \int_{E=0}^{\infty} I(E) dE = \int_{E=0}^{\infty} P(E) \exp\{-\mu_a(E) t_a - \mu_g(E) t_g\} dE \quad \text{[Expression 3]}$$

In the above described [Expression 3], $\mu_a(E)$ and $\mu_g(E)$ are attenuation coefficients of the adipose and the mammary glands corresponding to the incident X-ray spectrums, respectively.

Here, the average attenuation coefficient for the incident X-ray spectrum can be expressed by the following expression.

$$\bar{\mu} = \frac{\int_{E=0}^{\infty} \mu(E) I(E) dE}{\int_{E=0}^{\infty} I(E) dE} \quad \text{[Expression 4]}$$

When the average attenuation coefficient of the adipose is set as $\bar{\mu}_a$, the average attenuation coefficient of the mammary glands is set as $\bar{\mu}_g$, and in the situation where $\bar{\mu}_a$ and $\bar{\mu}_g$ smoothly change by the change of $t_a$ and $t_g$, the following expression can be established.

$$I = I_0 \exp\{-\bar{\mu}_a t_a - \bar{\mu}_g t_g\} \quad \text{[Expression 5]}$$

($I_0$ is a constant)

Further, when logarithms of both sides of the above described [Expression 5] are taken, the following expression is obtained.

$$\log(I) = \log(I_0) - \bar{\mu}_a t_a - \bar{\mu}_g t_g \quad \text{[Expression 6]}$$

When the pixel value of the X-ray image is assumed to be proportional to the logarithm of the X-ray dose, the pixel value I(x, y) in respective coordinates (x, y) of the breast image can be expressed by the following expression.

$$I(x,y) = I_0 - \bar{\mu}_a t_a(x,y) - \bar{\mu}_g t_g(x,y) \quad \text{[Expression 7]}$$

Here, the constant $I_0$ corresponds to the pixel value in a directly irradiated region, which is a region where there is no X-ray attenuation.

A mammary gland content rate G(x, y) desired to be obtained is the ratio of the thickness $t_g(x, y)$ of the mammary glands to the thickness ($t_a(x, y) + t_g(x, y)$) of the breast through which the X-ray passes, and can be expressed by the following expression.

$$G(x, y) = \frac{t_g(x, y)}{t_g(x, y) + t_a(x, y)} \quad \text{[Expression 8]}$$

Here, when an image (adipose image) A(x, y) with only the adipose tissue and free from the mammary glands is assumed, the adipose image A(x, y) can be expressed by the following expression.

$$A(x,y) = I_0 - \bar{\mu}_a (t_g(x,y) + t_a(x,y)) \quad \text{[Expression 9]}$$

When [Expression 7] and [Expression 9] are substituted into the above described [Expression 8] and organized, the mammary gland content rate G(x, y) can be rewritten to the following expressions.

$$G(x, y) = \frac{A(x, y) - I(x, y)}{I_0 - A(x, y)} * \frac{1}{\bar{\mu}_g / \bar{\mu}_a - 1} \quad \text{[Expression 10]}$$

-continued $$G(x, y) = \frac{A(x, y) - I(x, y)}{I_0 - A(x, y)} \times \frac{1}{\mu - 1}$$ [Expression 11]

[Expression 11] is the result of rewriting the ratio ($\bar{\mu}_a/\bar{\mu}_b$) of the average attenuation coefficient $\bar{\mu}_g$ of the mammary glands and the average attenuation coefficient $\bar{\mu}_a$ of the adipose in the expression of [Expression 10] to $\mu$. The presently disclosed subject matter estimates the mammary gland content rate G(x, y) from the [Expression 11].

In the above described [Expression 11], the pixel value I(x, y) of the breast image is the pixel value which is observed (observed pixel value).

Here, the observed pixel value is the value which is proportional to the logarithm of the transit dose, and therefore, the pixel value $I_0$ of the directly irradiated region where the transit dose becomes the maximum can be acquired by obtaining the maximum value out of the observed pixel values.

After that, if the adipose image A(x, y) shown in [Expression 9], and the ratio $\mu$ of the average attenuation coefficient of the mammary glands and the average attenuation coefficient of the adipose can be estimated, the mammary gland content rate G(x, y) can be estimated from the above described [Expression 11].

<Estimation of Average Attenuation Coefficient>

As is known from [Expression 3] and [Expression 4], the average attenuation coefficient is the value which changes in accordance with the spectrum of the incident X-ray and the thickness of the subject.

Figure 5:
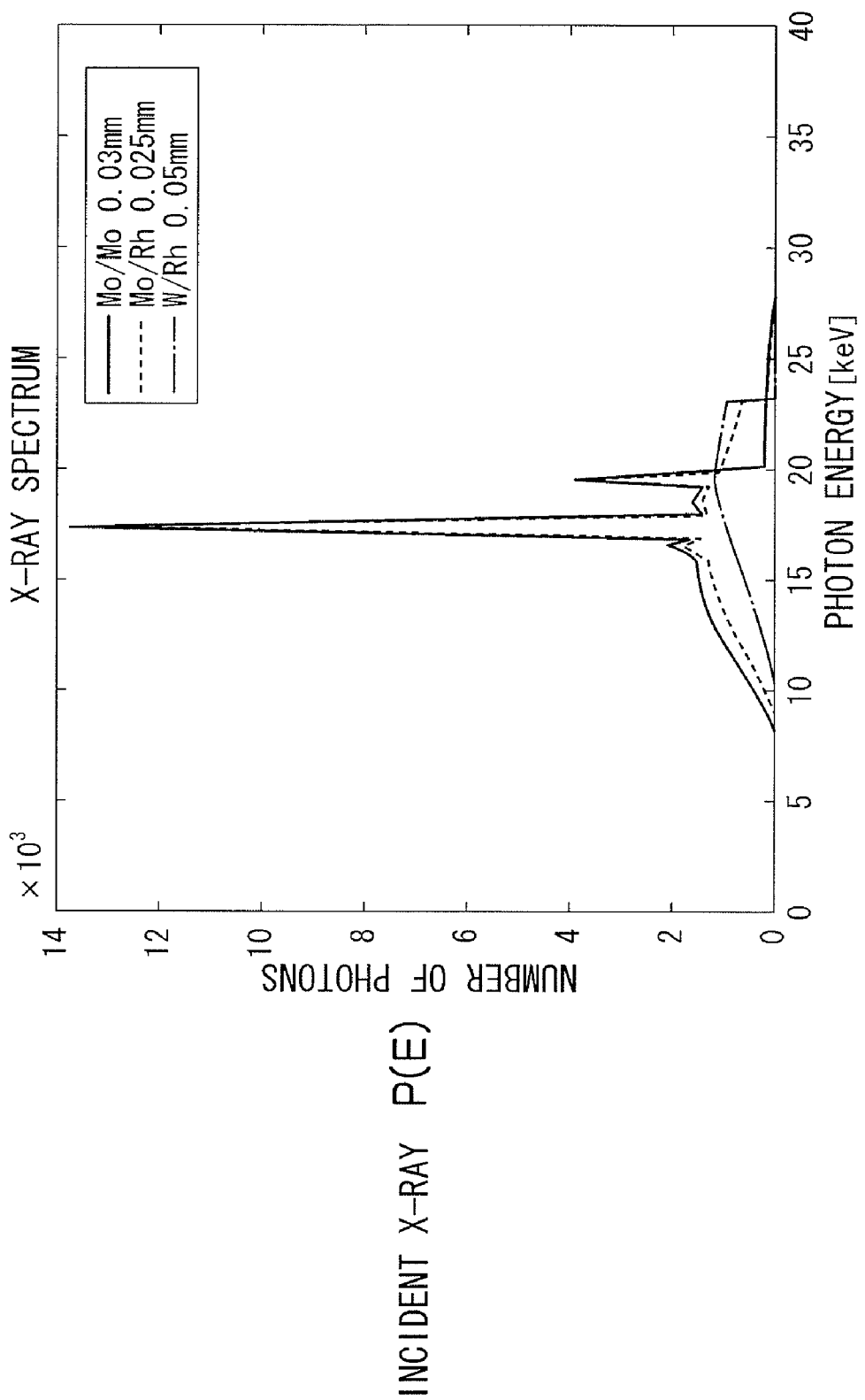
FIG. 5 is a graph showing three kinds of X-ray spectrums commonly used in mammography imaging.

Thus, as shown in FIG. 5, three kinds of X-ray spectrums which are commonly used in mammography imaging are assumed, and simulation of how the average attenuation coefficient changes is performed.

The spectrum of the incident X-ray has various characteristics in accordance with the combination of the target and the filter in the X-ray source. Three kinds of X-ray spectrums shown in FIG. 5 shows the case of using an MO (molybdenum) target/MO filter (0.03 mm), an MO target/Rh (rhodium) filter (0.025 mm), a W (tungsten) target/Rh filter (0.05 mm) as the target/filter combination, with the X-ray tube voltage set at 28 kV.

The thickness of the breast at the time of mammography imaging is about 4 cm in average, and the thickness is 2 cm when thin, whereas the thickness is about 8 cm when thick. The average attenuation coefficient $\bar{\mu}_g$ of the mammary glands and the average attenuation coefficient $\bar{\mu}_a$ of the adipose the difference of these average attenuation coefficients, and the ratio are calculated for the respective thicknesses and the three kinds of X-ray spectrums (three kinds of target/filter combinations) shown in FIG. 5.

FIG. 7 shows the calculation results.

From the table shown in FIG. 7, it is found out that the average attenuation coefficient is the value which significantly changes depending on the X-ray spectrum and the breast mass thickness.

However, the value of the ratio of the average attenuation coefficient $\bar{\mu}_g$ of the mammary glands and the average attenuation coefficient $\bar{\mu}_a$ of the adipose varies only in the range of ±5% of the reference value (1.778=0.80/0.45) with the mammary gland average attenuation coefficient $\bar{\mu}_g$=0.80 and the adipose average attenuation coefficient $\bar{\mu}_a$=0.45 as the references.

From [Expression 11] ([Expression 1]), the influence which the mammary gland content rate G(x, y) has on the calculation is in the range of ±10% with respect to the calculation result to which the above described reference value is applied. For example, if the mammary gland content rate is 50%, the error is in the range of 45% to 55%. More specifically, even if the fixed ratio of the average attenuation coefficients (the above described reference value) is used, the mammary gland content rate can be estimated without receiving much influence of the imaging conditions such as the X-ray spectrum and the breast mass thickness.

Meanwhile, in the method according to "Volumetric Breast Density Estimation From Full-Field Digital Mammograms", IEEE Trans. MEDICAL IMAGING, Vol. 25, No. 3, 2006 which estimates a mammary gland content rate by using the value of the difference of the average attenuation coefficient $\bar{\mu}_g$ of mammary glands and the average attenuation coefficient $\bar{\mu}_a$ of adipose, when the average attenuation coefficient $\bar{\mu}_g$ and the average attenuation coefficient $\bar{\mu}_a$ of adipose are fixed to reference values, the mammary gland content rate estimated by using the individual average attenuation coefficient $\bar{\mu}_g$ of mammary glands and average attenuation coefficient $\bar{\mu}_a$ of adipose according to each of the imaging conditions varies in the range of ±20 to 30%, with respect to the calculation result to which the reference values are applied.

When the composition of a breast is qualitatively classified, the breast composition is classified into four stages of: the adipose with a mammary gland content rate of lower than 10%; the scattered mammary gland with a mammary gland content rate of about 10 to 30%; the nonuniform high density with about 50 to 60%; and the high density with about 80 to 90%.

When an error of ±20 to 30% occurs to estimation of the mammary gland content rate, the above described classification is likely to change. Therefore, the precision is insufficient for the quantitative evaluation. Thus, it is necessary to acquire information concerning imaging and information of breast mass thickness, and calculate the average attenuation coefficients of the mammary glands and adipose each time.

In contrast with this, when the estimation error of the mammary gland content rate is in the range of ±10%, the above described classification does not change, and the precision is sufficient for the quantitative evaluation.

Figure 6:
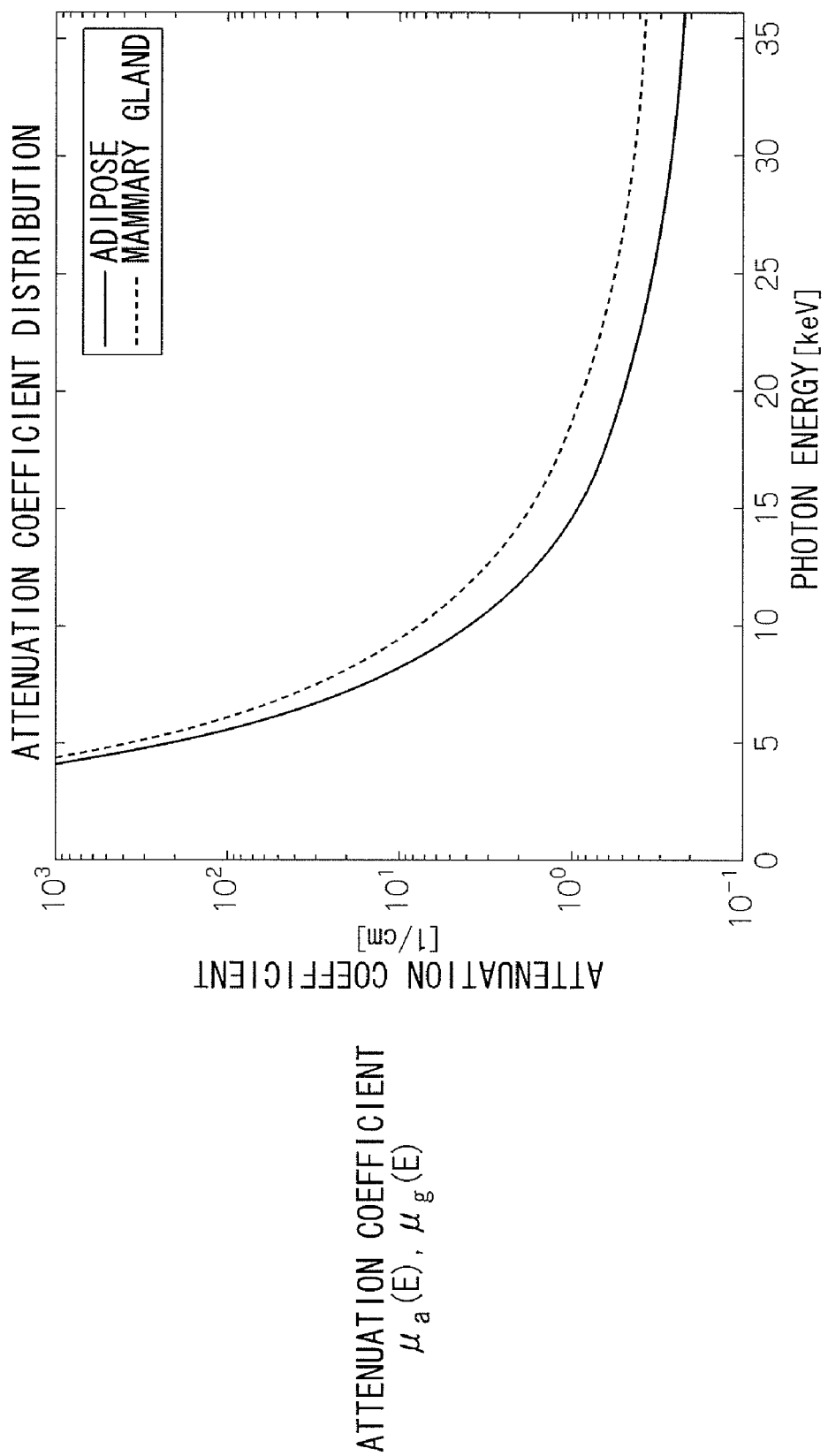
FIG. 6 is a graph showing attenuation coefficients of mammary gland and adipose with respect to photon energy.

In the simulation, the measurement results by Johns and Yaffe shown in the graph of FIG. 6 were used as the attenuation coefficients of the mammary glands and adipose. (Johns P C, Yaffe M j, "X-ray characterization and neoplastic Breast tissues", Phy Med Biol. Vol. 32, pp. 675-695, 1987.)

As shown in FIG. 6, with respect to the photon energy, the attenuation coefficient $\mu_g(E)$ of the mammary gland tissue is the value larger than the attenuation coefficient $\mu_a(E)$ of the adipose tissue.

<Estimation of Adipose Image>

In order to obtain the mammary gland content from [Expression 11] ([Expression 1]), the adipose image A(x, y) needs to be estimated.

The adipose image A(x, y) is the image with only adipose tissues without presence of mammary glands, and the aforementioned [Expression 9] can be expressed by the following expression when the breast mass thickness in the respective coordinates (x, y) of the breast image is set as T(x, y).

$$A(x, y) = I_0 - \bar{\mu}_a \underbrace{(t_a(x, y) + t_g(x, y))}_{=T(x,y)}$$ [Expression 12]

Incidentally, a breast is imaged by being compressed as shown in FIG. 3. Therefore, the thickness of a part of the breast corresponds to the space between the imaging table 122 and the compression plate 124, but the thickness of the breast in the range enclosed by circle C in FIG. 3 does not correspond to the space between the imaging table 122 and the compression plate 124.

However, when it is assumed that the breast mass thickness in this part is determined by a distance "d" (hereinafter, called "skin line distance") in the direction of the normal line from a skin line (contour line of the breast) showing the boundary between the breast region and the directly irradiated region, [Expression 12] can be rewritten to the following expression.

$$A(d) = I_0 - \bar{\mu}_a T(d) \qquad \text{[Expression 13]}$$

More specifically, by the distance "d" from the skin line, the pixel value in the case of the adipose tissue of 100% can be estimated.

Actually, in the pixels on the line showing distance "d" from the skin line, pixels with only the adipose tissue and pixels with presence of both the mammary glands and adipose are present.

Figure 8:
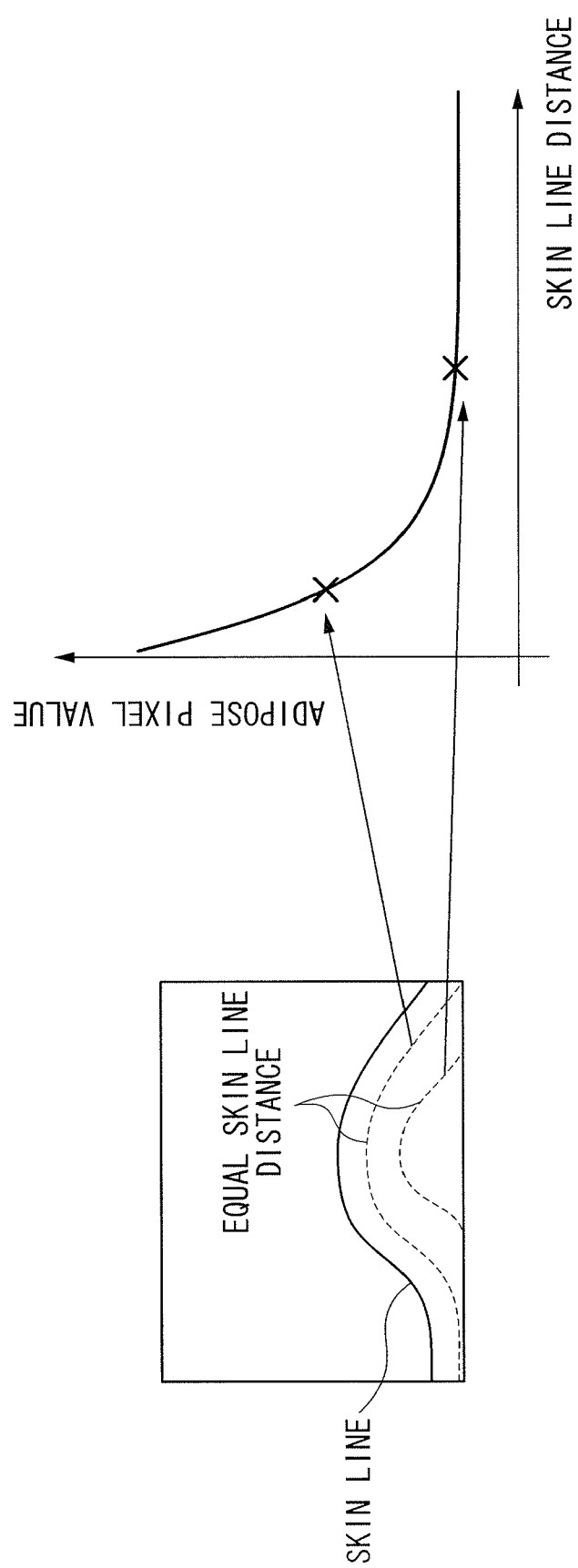
FIGS. 8A and 8B are diagrams showing the relationship of a skin line distance and an adipose pixel value.

Thus, as shown in FIGS. 8A and 8B, from the pixels with an equal distance from the skin line (pixels with equal skin line distance), the representative values representing the adipose pixel values of the pixels with the equal skin line distance are calculated, the aforementioned calculated representative values are plotted on the XY coordinates with the skin line distance (that is, distance from the skin line) set as the X axis and the adipose pixel value set as the Y axis, and the curve passing through the plotted points is obtained, whereby the relationship between the skin line distance and the adipose pixel value can be estimated. Details of this will be described later.

Regarding pixel value of the adipose image in certain coordinates (x, y), the skin line distance at the coordinates (x, y) is obtained, and then the adipose pixel value is estimated from the obtained skin line distance.

Subsequently, by substituting the pixel value I(x, y) of the observed breast image, the pixel value $I_0$ of the directly irradiated region, the predetermined value μ (=1.778) showing the ratio of the average attenuation coefficients of the mammary glands and adipose, and the pixel value A(x, y) of the adipose image into the aforementioned [Expression 11] ([Expression 1]), the mammary gland content rate G(x, y) can be estimated with high precision for each pixel. Further, at this time, the values for calculating [Expression 1] can be obtained from only the image data of the breast image without acquiring the information on the imaging conditions and the like, and thus, the mammary content rate can be estimated.

[Estimation of Volume Ratio of Mammary Glands]

When the volume of the mammary glands is set as $V_g$, and the volume of the entire breast is set as V, the volume ratio of the mammary glands can be expressed by the following expression.

$$\frac{V_g}{V} = \frac{\sum t_g(x, y)}{\sum T(x, y)} \qquad \text{[Expression 14]}$$

Here, it is difficult to obtain the volume $V_g$ of the mammary glands and the volume V of the entire breast directly, but the volume ratio can be estimated by using the mammary gland content rate G(x, y).

More specifically, [Expression 12] can be transformed into the following expression.

$$\bar{\mu}_a T(x,y) = I_0 - A(x,y) \qquad \text{[Expression 15]}$$

Accordingly, if the weighted average of the mammary gland content rate G (x, y) is obtained as the following expression with ($I_0$-A(x, y)) as the weight from the expressions of [Expression 8], [Expression 14] and [Expression 15], the volume ratio of the mammary glands can be estimated.

$$\frac{V_g}{V} = \frac{\sum G(x, y) * T(x, y)}{\sum T(x, y)} = \frac{\sum G(x, y) * (I_0 - A(x, y))}{\sum (I_0 - A(x, y))} \qquad \text{[Expression 16]}$$

[Mammary Gland Content Rate Estimating Method]

Next, an embodiment of the mammary gland content rate estimating method according to the presently disclosed subject matter will be described.

Figure 9:
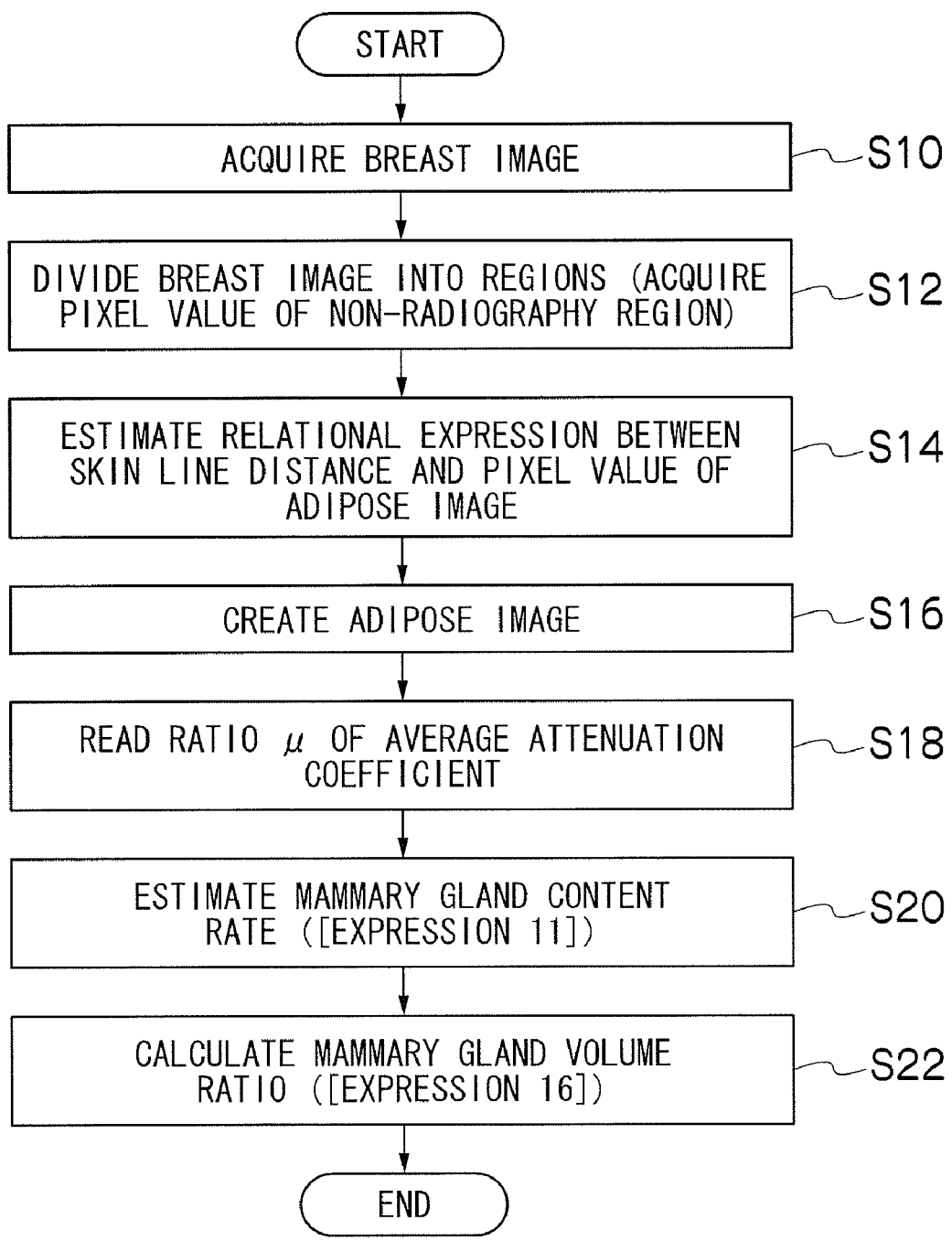
FIG. 9 is a flowchart showing a method for estimating mammary gland content rate according to an embodiment of the presently disclosed subject matter.

As shown in FIG. 9, the CPU 12 of the mammary gland content rate estimating apparatus 10 acquires the breast image for which the mammary gland content rate is estimated (step S10). As for this breast image, the image file of the breast image stored in the image DB 44 may be acquired from the image DB 44 via the network 50 based on input of the subject ID or the like, or the breast image may be automatically acquired from the mammography imaging apparatus 40 via the network 50 after the image is taken by the mammography imaging apparatus 40. In order to enhance the speed of the subsequent analysis processing, the acquired breast image is desirably reduced.

<Estimation of Adipose Image>

Figure 10A:
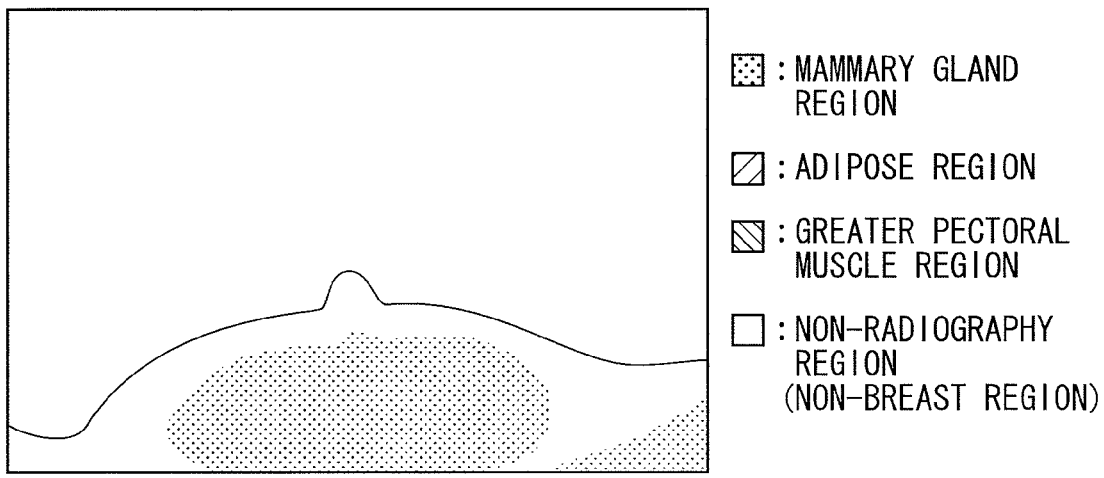
FIG. 10A is a diagram showing an original image of a breast image.
Figure 10B:
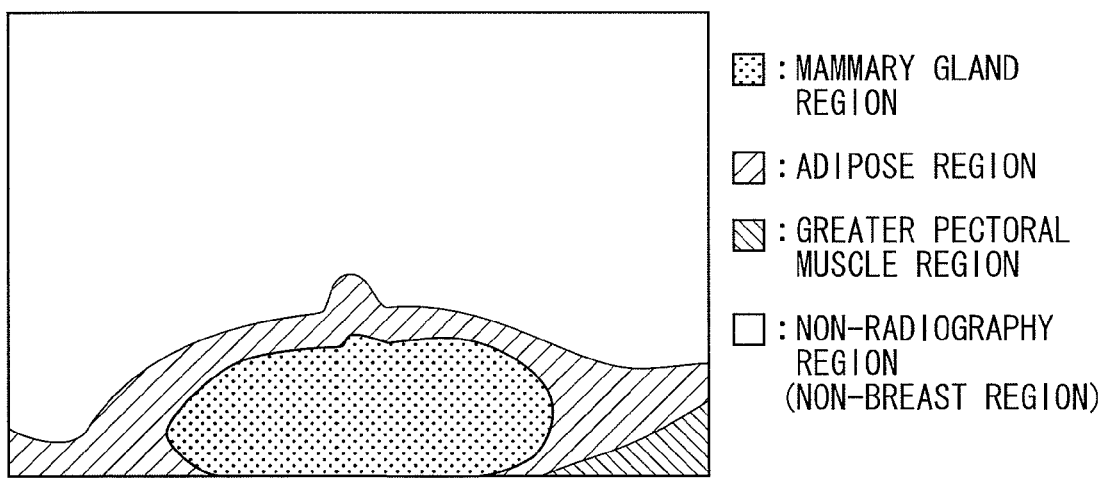
FIG. 10B is a diagram showing an image divided into regions of respective structures extracted from the original image.

Subsequently, the CPU 12 estimates the adipose image from the acquired breast image (steps S12 to S16). In order to estimate the adipose image, the breast image is divided into regions (step S12). As shown in FIGS. 10A and 10B, in the division of the breast image into regions, based on the breast image (FIG. 10A), the breast image is divided into the regions of the respective structures (a whole breast region, a mammary gland region, an adipose region, a greater pectoral muscle region and a directly irradiated region (non-breast region)) (see FIG. 10B).

However, it is impossible to separate the respective structures which three-dimensionally overlay one another accurately from the two-dimensional image. What is important here is not accurate separation of the respective structures, but extraction of the pixels which are considered to be surely composed of only adipose tissue. One method for this will be shown in the following. (For details, see Japanese Patent Application Laid-Open No. 2005-65855 filed by the present applicant).

(i) An image is divided into a breast region and a directly irradiated region. Since the directly irradiated region especially exhibits a high density on the image, the peak which appears at the high density side in the density histogram of the entire image corresponds to the directly irradiated region. By performing binarization with the value obtained by subtracting a fixed value from the peak value set as a threshold value, the image is divided into the breast region and the directly irradiated region. Alternatively, binarization may be performed by scanning the breast image from the high density side in the density histogram and by setting a point with the predetermined value or smaller first as a threshold value. For calculation of mammary gland content rate, the above described peak value is acquired and held as the pixel value $I_0$ of the directly irradiated region.

(ii) The skin line which is the contour of the breast region is extracted. The boundary points of the breast region and the directly irradiated region are sequentially searched (scanned) for, and the pixels searched for are connected, whereby the skin line can be extracted.

(iii) The greater pectoral muscle region is extracted. Since the edge of the boundary of the greater pectoral muscle region and the adipose region is relatively clear, scanning by a differential operator is performed toward the chest wall side from the skin line, and the points having large differential values are extracted as the boundary points of the greater pectoral muscle region. The curve connecting the extracted boundary points is calculated, and the chest wall side (opposite side from the directly irradiated region) with respect to the curve is extracted as the greater pectoral muscle region.

(iv) The threshold value for separating the mammary glands and the adipose region is calculated from the density values of the greater pectoral muscle region and the adipose region in the vicinity of the greater pectoral muscle region. By performing parameter setting so that the threshold value becomes a little larger value, the pixels surely composed of only the adipose tissue can be extracted.

When the region dividing of the breast image is performed as described above, the relational expression between the skin line distance and the pixel value of the adipose image is estimated next (step S14 of FIG. 9).

Figure 11:
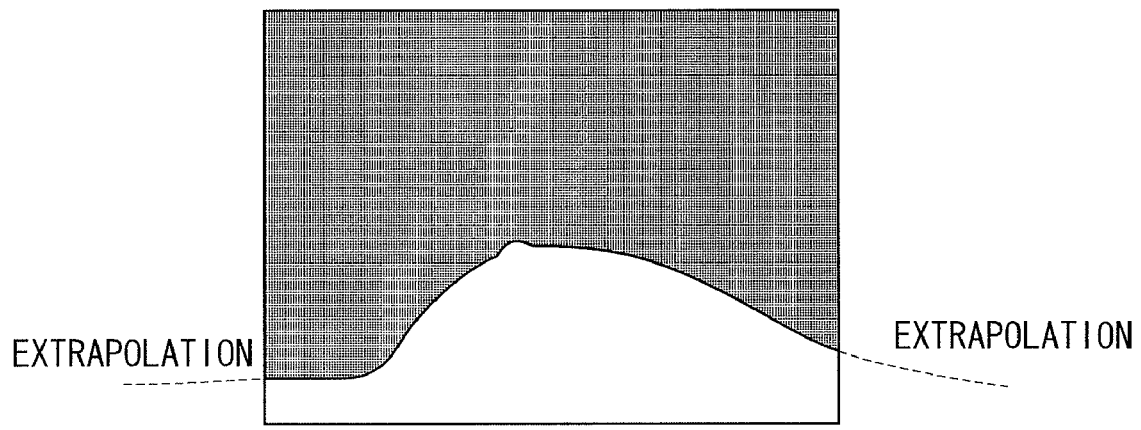
FIG. 11 is a diagram used for explaining extension of a skin line.

(v) As shown in FIG. 11, in order to consider the skin line of the breast region which is cut at the image ends, the skin line is extended in accordance with necessity (the shape of the skin line is extrapolated). Extrapolation of the skin line is performed by performing linear approximation by the method of least squares by using the coordinate values of ten points from the ends, for example, at each of the right end and the left end.

(vi) In each pixel, the shortest distance (Euclidean distance) to the skin line is calculated. Here, for shortening the processing time, it is desirable that the shortest distance is roughly (ten pixels skip) searched for at first, and thereafter, the periphery of the shortest distance is further searched (scanned) for minutely.

(vii) In each of the skin line distances, the pixel values of a plurality of adipose pixels are collected, and the median value of these pixel values is calculated. As a representative value of the pixel values of the plurality of adipose pixels, the average value, the mode value, the extremal value and the like are conceivable without being limited to the median value.

Figure 12:
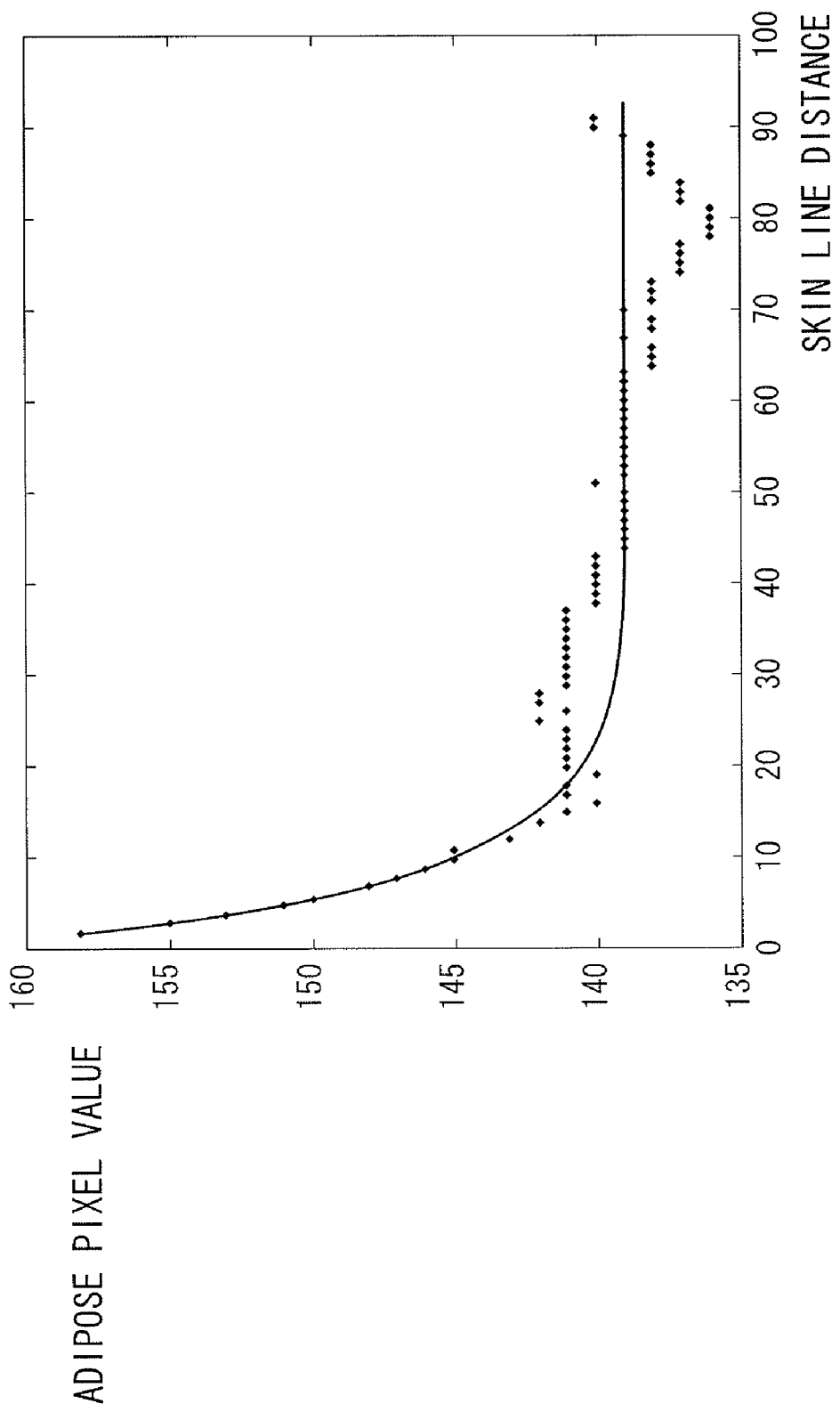
FIG. 12 is a graph in which an adipose pixel value is plotted at each skin line distance.

FIG. 12 shows a graph in which an adipose pixel value is plotted with respect to skin line distance. In FIG. 12, the X-axis indicates the skin line and the unit of the skin line distance is "pixel."

(viii) The relational expression between the skin line distance (distance from the skin line) and the adipose pixel value is estimated by curve approximation. In concrete, a curve Y is assumed to be the following expression, $$Y = a * \exp(-bx) + c \quad \text{[Expression 17]}$$

(where X: skin line distance, Y: adipose pixel value), and the coefficient is estimated by the simplex method. As for the initial value, a=(the maximum value of the pixel value)−(the minimum value), b=10/the maximum distance from the skin line (empirical value), and c=the minimum value of the pixel value.

(ix) By substituting the skin line distance of each pixel in the breast image into [Expression 17], the pixel value of the adipose image is calculated, and thereby, the adipose image is created (step S16). The creating method of the adipose image is not limited to the above description, and the adipose image may be obtained by using smoothing processing as in "Thickness correction of mammographic images by anisotropic filtering and interpolation of dense tissue", Proc. SPIE (Medical Imaging: Image Processing), Vol. 5747, pp. 1521-1527, 2005.

Next, the CPU 12 reads the predetermined value μ (=1.778, for example) expressing the ratio of the average attenuation coefficients of the mammary glands and adipose which are stored in the hard disk device 20 or the nonvolatile memory not illustrated (step S18).

Subsequently, the CPU 12 substitutes the pixel value I(x, y) of the breast image acquired in step S10, the pixel value $I_0$ of the directly irradiated region acquired in step S12, the pixel value A(x, y) of the adipose image created in step S16 and the ratio μ of the average attenuation coefficients stored in advance into [Expression 11] ([Expression 1]), and thereby, calculates the mammary gland content rate G(x, y) for each of the respective pixels of the breast image (step S20).

When the mammary gland contents rate G(x, y) of all the pixels of the breast image are calculated, the weighted average of the calculated mammary gland content rates G(x, y) is obtained using $(I_0 - A(x, y))$ as the weight (see the expression of [Expression 16]), and thereby, the volume ratio of the mammary glands is estimated (step S22).

APPLICATION EXAMPLE (1) Display of Mammary Gland Content Rate or Volume Ratio of Mammary Glands The mammary gland content rate or the volume ratio of the mammary glands which is calculated as described above may be displayed on the screen of the monitor device. Since the mammary gland content rate can be obtained for the respective pixels, the mammary gland content rate may be displayed in a two-dimensional image form or a graphical form (histogram). Further, one value of the volume ratio of the mammary glands can be obtained for one image, and therefore, the value may be displayed with the image. The information of them is stored in the header of the DICOM file, and can be stored in the image DB 44 together with the taken image. When a doctor interprets the image, the taken image is displayed, and the information of them is displayed at the same time to be the assistance for diagnosis.

(2) Application to Computer-Aided Diagnosis (Computer-Aided Diagnosis: CAD)

Appearance of a lesion differs between the region with high mammary gland content rate and the region with low mammary gland content rate, and therefore, the detection algorithm is desirably changed. Further, when the volume ratio of the mammary glands is high, it can be said that a doctor is highly likely to miss a lesion, the number of lesions detected may be made large.

(3) Application to Image Processing

As the volume ratio of the mammary glands is higher, the contrast of the mammary glands becomes lower, and a lesion becomes more difficult to find in the image. Therefore, the contrast enhancement degree may be changed in accordance with the volume ratio of the mammary glands.

Further, the mammary gland content rate can be estimated for respective pixels, and therefore, more detailed image analysis can be made. For example, from the mammary gland content rate, the region with more mammary glands and the region with less mammary glands can be distinguished. Therefore, the pixel value and the contrast value in the region with more mammary glands are calculated, and used for setting of the image processing conditions. In concrete, histogram analysis is performed by using only the pixels with the mammary gland content rate of a predetermined threshold value or larger, and the image processing conditions is set based on the analysis result. Further, the mammary gland content rates may be used as weights, and the weighted histogram of the entire breast may be created to perform histogram analysis. Further, contrast calculation may be performed by the method other than histogram analysis. The weighted average value may be calculated by using the mammary gland content rate as weights with respect to the contrast value obtained in the peripheral region of each of the pixels, and the mammary gland contrast value of the entire breast image may be calculated. In the setting of the image processing conditions, the shift amount of the gradation can be determined so that the calculated pixel value of the mammary gland region becomes a predetermined value, and/or the inclination of the gradation can be determined in accordance with the calculated contrast value. Further, the pixel value and the contrast value may be used not only for setting of the gradation processing conditions, but also for setting of the frequency enhancement processing conditions. However, the frequency band of lesions includes diverse frequencies ranging from a low frequency (tumor) to a high frequency (calcification), and therefore, it is more desirable to perform contrast enhancement by gradation processing than to enhance a specific frequency band.

Hereinafter, the method for calculating the pixel value and the contrast value which are described above will be described in more detail. In this method, the tissue structures (mammary gland, adipose) of the breast image are analyzed, and based on the analysis result, the image processing conditions suitable for the image are set, and the density/contrast is controlled.

In the conventional processing for a breast image, the image processing is performed by setting the typical conditions (hereinafter, called the standard conditions) which are set beforehand so that the image suitable for image interpretation is obtained. However, depending on the difference in the physical constitutions of patients and difference in the mammary gland content rates (individual differences), the image which is processed under the standard conditions is sometimes insufficient for the radiogram interpretation capability.

According to the presently disclosed subject matter, more detailed image analysis is enabled, and therefore, setting of the image processing conditions corresponding to the individual difference is enabled. The main differences from the conventional processing according to the standard conditions are the following three respects.

(1) The mammary gland density is controlled based on the extraction result of the mammary gland region.
(2) In accordance with the dynamic range of each image, intensity of the dynamic range compression processing is controlled.
(3) In accordance with the local contrast values in the mammary glands, the inclination of gradation is controlled.

FIG. 13 shows the flow of the image analysis processing. FIGS. 14A to 14G illustrate the breast images processed in the image analysis processing.

Figure 14A:
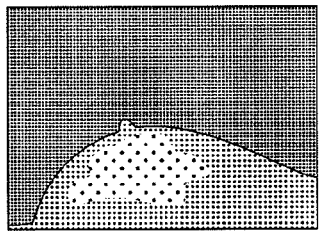
FIGS. 14A to 14G are images used in the image analysis processing shown in FIG. 13.
Figure 14B:
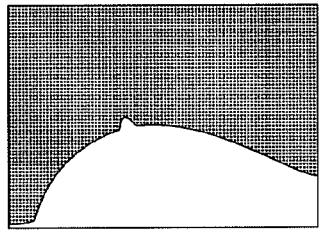

First, in step S30 of FIG. 13, as in step S10 of FIG. 9 which is described above, the CPU 12 of the mammary gland content rate estimating apparatus 10 receives the breast image which is the original image (original breast image). FIG. 14A shows an example of the original breast image. Next, in step S32, the original breast image is divided into a breast region and a directly irradiated region, and a breast region mask is extracted. FIG. 14B shows an example of the breast region mask. As described above, the skin line which is the contour of the breast region is extracted at this time. The boundary points between the breast region and the directly irradiated region are sequentially searched (scanned) for. By connecting the pixels which are searched for, the skin line can be extracted, and the skin line pixel values are obtained.

Figure 14C:
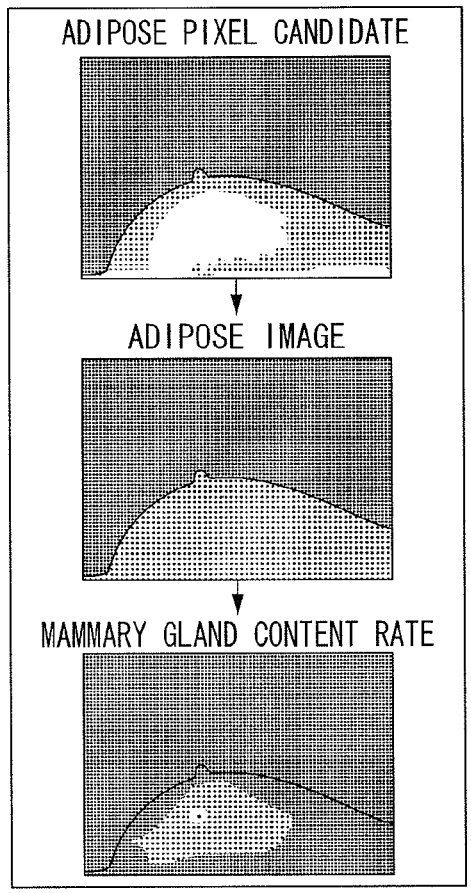

Next, the process is divided into two. In step S34, the mammary gland content rate estimation processing is performed, whereas in step S36, the mammary gland presence probability map estimation processing is performed. Here, in the mammary gland content rate estimation processing of step S34, adipose pixel candidates is obtained by using the original breast image and the breast region mask, the adipose image is created, and the mammary gland content rate is estimated. FIG. 14C shows examples of the adipose pixel candidate, adipose image, and the image of mammary gland content rates. The processing is included in the processing described with FIG. 9 which is described above, and therefore, the detailed description will be omitted here.

Figure 14D:
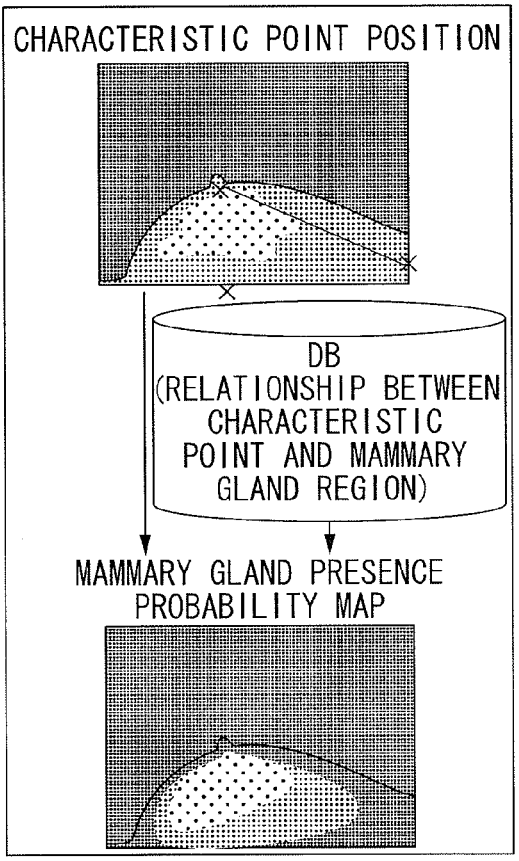
Figure 15:
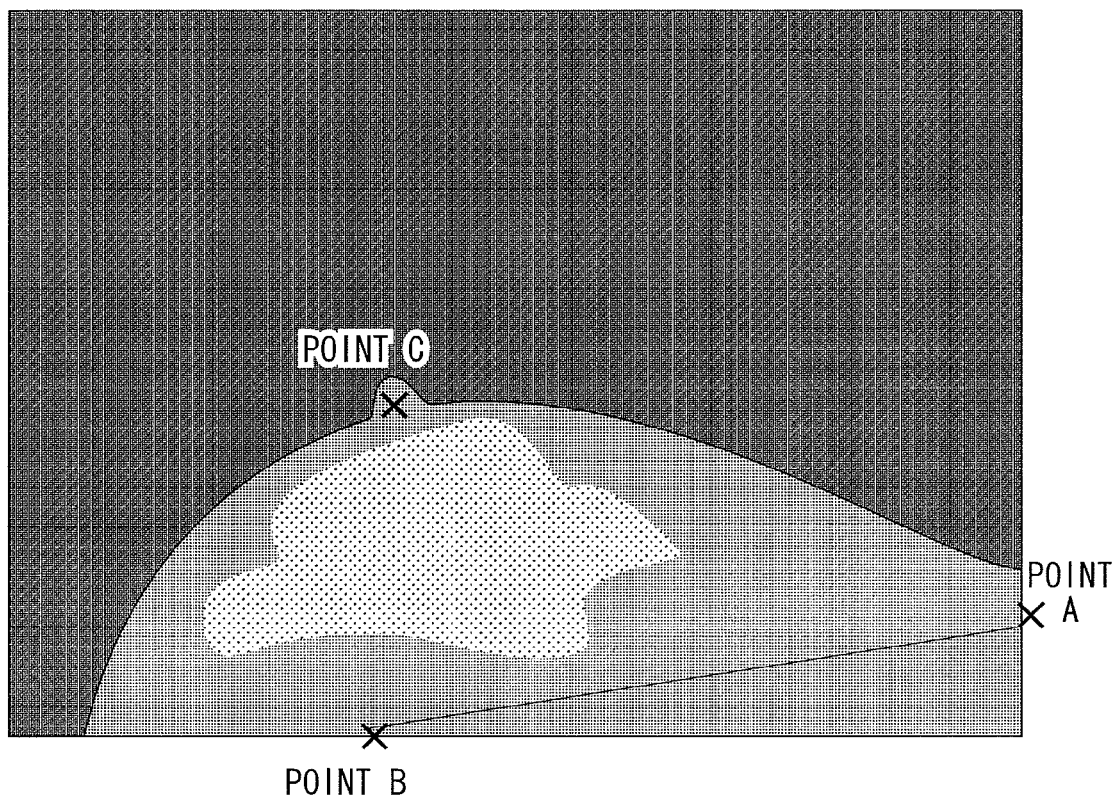
FIG. 15 is an explanatory view showing a state of detecting characteristic points from a breast image.
Figure 17:
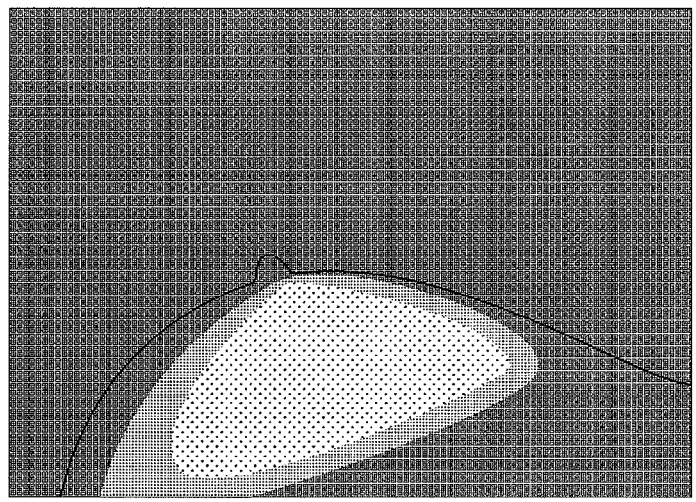
FIG. 17 is an explanatory view showing one example of a mammary gland presence probability map.

In the mammary gland presence probability map estimation processing in step S36, characteristic point positions are obtained from the breast image, and the mammary gland presence probability map is estimated by using the relationship between the characteristic points and the mammary gland region, which is previously stored in the database. FIG. 14D shows examples of an image from which characteristic point positions are extracted (the larger image is shown in FIG. 15), and the mammary gland presence probability map (the larger image is shown in FIG. 17).

First, detection of the characteristic points (anatomical characteristic points) will be described. As shown in FIG. 15, in the breast image, as the characteristic points, the three characteristic points are detected, which are two points A and B on the boundary line expressing the boundary line between the greater pectoral muscle and the adipose region, and point C on the skin line expressing the position of a nipple.

As described above, the breast region is divided into a mammary gland region, an adipose region and a greater pectoral muscle region. The edge of the boundary between the greater pectoral muscle region and the adipose region is relatively clear, and both ends on the image on this boundary are set as points A and B.

Further, as the point C which expresses the position of the nipple, the position of the nipple (corresponding position) may be detected as the structure in the breast image by applying template matching using a template to the breast image based on the template corresponding to the structure (nipple) by referring to the lookup table and the like stored in advance, for example. Or, the position (point C) may be detected based on instruction by a radiogram interpreter with a cursor linked to a mouse to select the structure (nipple) using a rectangular frame (ROI frame) in the breast image. Further, the point C may be detected by detecting the boundary line between the breast and the transparent portion by edge detection or the like, and setting the point (vertex of the boundary line in a semicircular shape) at which the distance from the image end at the chest wall side is the longest in the boundary line, as the nipple position.

Subsequently, in each of the pixels in the subject, the distance from the skin line and the distance from the point C are calculated. At this time, the distance (the length of the perpendicular line descending from C to meet the line AB) between a line AB expressing the greater pectoral muscle and the point C is normalized to be one.

Figure 16:
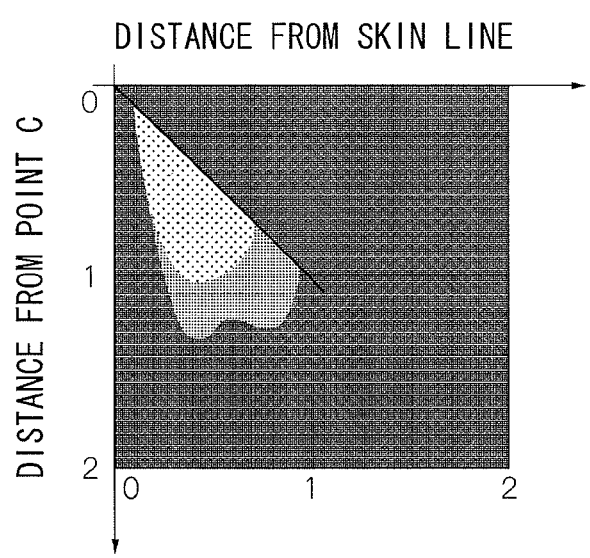
FIG. 16 is an explanatory view showing one example of a mammary gland presence probability obtained with a large amount of data.

Meanwhile, the mammary gland presence probabilities showing the relationship between the characteristic points and the mammary gland region are stored in the database DB from a large quantity of data in advance. FIG. 16 shows one example of the mammary gland presence probability obtained from a large amount of data. In FIG. 16, the axis of abscissa shows the distance of each point from the skin line, and the axis of ordinates shows the distance of each point from the point C. Because the skin line distance and the distance from the point C have been normalized in FIG. 16 (and in FIG. 17 as well), the X-axis and the Y-axis have no units. In FIG. 16, a lower (whiter) density shows a higher probability of presence of the mammary glands.

Next, by using the mammary gland presence probabilities which are stored in the database in advance based on a large amount of data, a mammary gland presence probability map is created, in which the mammary gland presence probabilities is shown in an associated manner with the respective points (pixels) in the breast region in accordance with the distances from the characteristic point C and the skin line which are obtained above.

FIG. 17 shows one example of the mammary gland presence probability map. After all, the mammary gland presence probability map shown in FIG. 17 is the result of mapping the mammary gland presence probability shown in FIG. 16 so as to correspond to each of the points of the breast region in accordance with the distances from the characteristic point C and the skin line.

By using the mammary gland presence probability map thus created, the region which is likely to be mammary gland can be extracted more reliably. For example, the several pixels in the vicinity of the skin line tend to have large estimation errors of the mammary gland content rate, but the mammary gland presence probability map can compensate them.

As an application example using the mammary gland presence probability map, for example, when the average mammary gland content rate is calculated for a breast image, the weighted average is obtained using the mammary gland presence probability as the weight, and/or, as will be described later, the weight map in which the mammary gland content rate image and the mammary gland presence probability map are multiplied. This enables to calculate the mammary gland pixel value and the mammary gland contrast value, in a region with a high weight.

Figure 14E:
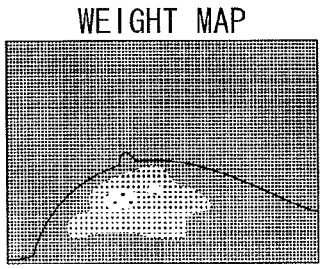
Figure 14F:
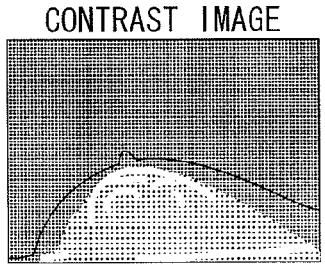
Figure 14G:
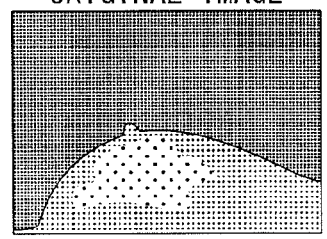

More specifically, in the next step S38, the weight map is created by multiplying the mammary gland content rate image and the mammary gland presence probability map. FIG. 14E shows an example of the weight map.

Subsequently, in step S40, by using the weight map and the contrast image, an average value is obtained from the weighted histogram, and thereby, the mammary gland contrast value is calculated. Here, the contrast image is the result of calculating the dispersion value of the pixel values in the peripheral region as the contrast values of each of the pixels in the original image. FIG. 14E shows an example of the contrast image. Further, in step S42, by using the weight map and the breast image which is the original image, the mammary grand pixel value is calculated from the weighted histogram. As the mammary gland pixel value, the pixel value of a whiter portion in the mammary glands is desirably calculated. The accumulation histogram is further created from the weighted histogram, and the 10% point of the accumulation frequency is calculated as the mammary gland pixel value. Specifically, first, the accumulation histogram which shows accumulation frequency (from 0% to 100%) against pixel value is created. The accumulation frequency is counted (accumulated) from the lowest pixel value to the highest pixel value. That is, the lower pixel value is, the lower accumulation frequency corresponding to the pixel value becomes. After that, the pixel value corresponding to the accumulation frequency of more than 10% is obtained as the pixel value of the mammary glands (mammary gland pixel value).

By controlling the parameter of the gradation conversion and the parameter of the dynamic range compression processing by using the three values (the mammary gland contrast value, the mammary gland pixel value, and the skin line pixel value) which are obtained as above, setting of the image processing conditions is performed.

Figure 18:
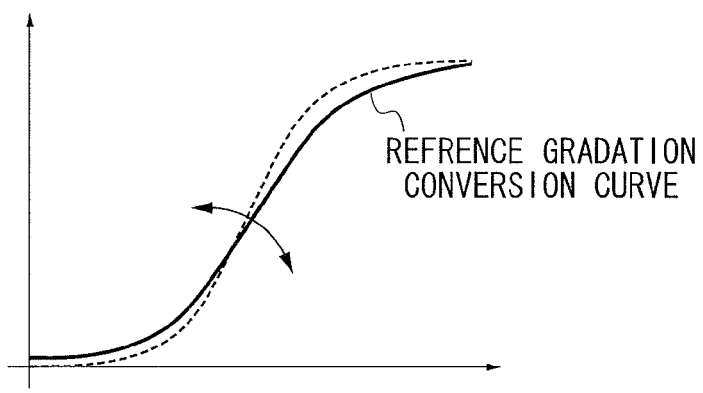
FIG. 18 is an explanatory diagram showing control of a gradation of a mammary gland contrast value.
Figure 19:
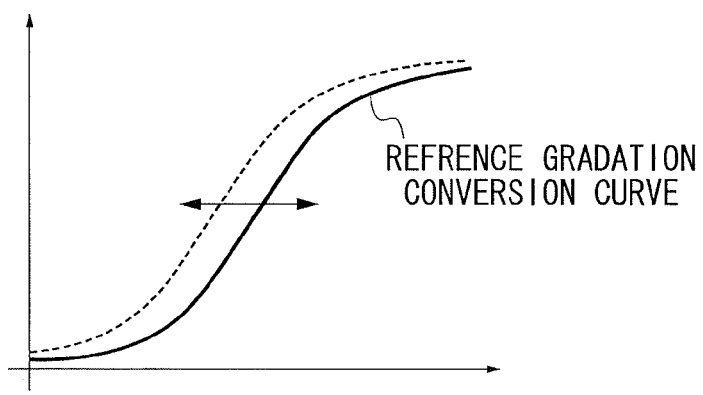
FIG. 19 is an explanatory diagram showing control of a gradation of a mammary gland pixel value.
Figure 20:
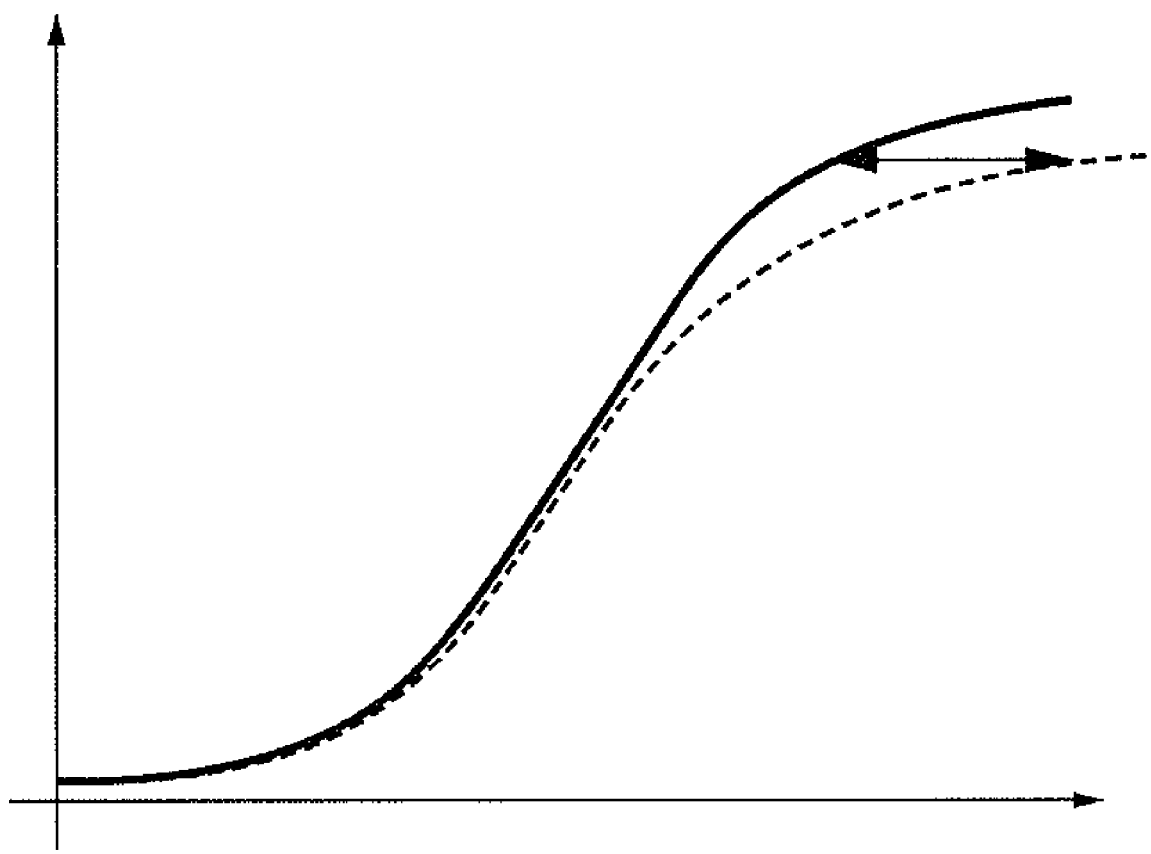
FIG. 20 is an explanatory diagram showing control of a gradation of a skin line pixel value.

FIGS. 18 to 20 explain how to control the gradation of mammary gland contrast value, the gradation of mammary gland pixel value, and the gradation of skin line pixel value, respectively. In each of FIGS. 18 to 20, the X-axis indicates the input pixel value and the Y-axis indicates output pixel value.

For example, as to the mammary gland contrast value, as shown in FIG. 18, when the mammary gland contrast value is low, the inclination of the gradation is controlled so that the contrast is made larger by making the inclination of the gradation larger with respect to a reference gradation conversion curve as shown by the broken line in the drawing.

Further, for example, as to the mammary gland pixel value, as shown in FIG. 19, the gradation shift amount is controlled so that the reference gradation conversion curve is parallel shifted as shown by the broken line in the drawing so that the density of the mammary gland region falls within a predetermined range.

Further, for example, as to the skin line pixel value, as shown in FIG. 20, the compression rate of the dynamic range is controlled so that the density of the skin line falls within a predetermined range. The dynamic range of the high density portion is desirably changed to be compressed without especially changing the low density portion.

(4) Application to Dose Control

An average glandular dose (AGD) which is generally used as the evaluation of exposure dose is usually calculated based on the mammary gland content rate of 50%. By calculating the mammary gland content rate from an image, a more accurate evaluation of an average glandular dose is enabled. Further, in order to calculate the mammary gland content rate for each of the pixels, not only the average glandular dose but also the maximum glandular dose may be calculated.

(5) Application to QA (Quality Assurance)

The region having a specific mammary gland content rate can be extracted, and therefore, by estimating the noise amount in the region having a certain mammary gland content rate and by comparison with the suitable noise amount which is previously determined, it becomes possible to determine whether the radiographic dose is suitable or not. Estimation of the noise amount can be calculated using the dispersion value of a high frequency component, for example. When the noise amount becomes a certain threshold value or larger, and it is determined as unsuitable, warning display is performed to urge the radiographic technician to take an image again.

[Others]

In this embodiment, the pixel value of a breast image is set as the value proportional to the logarithm of the transit dose, but even if the pixel value is the value inversely proportional to the logarithm of the transit dose, the aforementioned [Expression 1] is established. In this case, the pixel value of the directly irradiated region can be obtained by obtaining the minimum value of the observed pixel values. Further, as the input breast image, the image data including RAW data or the like, for which image processing such as gradation conversion of is not performed, is preferable. However, it is preferred that correction processing for uniformalizing the irradiation intensity distribution of X-rays which becomes nonuniform due to the heel effect and line width broadening, is applied to the input image.

Further, in this embodiment, as the method for extracting the pixels which seem to be composed of only the adipose tissue from the breast image, the method using a greater pectoral muscle region is shown. However, it is possible that there is no greater pectoral muscle in the breast image. Therefore, for more convenience, threshold value processing may be performed for the pixel values by using a known threshold determining method (determination analysis) without extracting a greater pectoral muscle region.

Further, in this embodiment, the thickness of the breast under the average imaging conditions is assumed, and 0.80/0.45=1.778 in the case of the mammary gland average attenuation coefficient being set as 0.80 and the adipose average attenuation coefficient being set as 0.45 is set as the predetermined attenuation coefficient ratio, but the ratio of the average attenuation coefficient is not limited to this, and the representative values such as the median value, the average value and the mode value among a plurality of ratios ($\overline{\mu}_g/\overline{\mu}_a$) of the average attenuation coefficients calculated under each of various imaging conditions as shown in the table of FIG. 7 may be adopted as the ratio of the average attenuation coefficients.

Further, it goes without saying that the presently disclosed subject matter is not limited to the above examples, and various improvements and modifications may be made within the range without departing from the spirit and scope of the presently disclosed subject matter.

For example, a recording medium (for example, a ROM, flexible disk, optical disk, and so on) storing a program including computer-executable instructions for causing one or more computers to execute steps of mammary gland content rate estimating method according to any one of the embodiments, can also achieve the aim of the presently disclosed subject matter. In this case, first, the program is installed to the one or more computer from the recording medium, and then the computer executes the program to perform the steps of the mammary gland content rate estimating method.

What is claimed is:

1. A mammary gland content rate estimating apparatus, comprising:
    a breast image acquiring device which acquires a breast image obtained by radiographing a breast by a mammography imaging apparatus;
    an adipose image estimating device which estimates an adipose image from the acquired breast image based on an assumption that an entire breast is composed of only adipose tissues;
    a device which acquires a pixel value of a directly irradiated region from the acquired breast image; and
    a mammary gland content rate calculating device which calculates a mammary gland content rate for each of pixels in the breast image based on the acquired breast image, the estimated adipose image and the acquired pixel value of the directly irradiated region.

2. The mammary gland content rate estimating apparatus according to claim 1, further comprising:
    a storage device which stores a predetermined value indicating a ratio of average attenuation coefficients of mammary glands and adipose,
    wherein the mammary gland content rate calculating device calculates the mammary gland content rate for each of the pixels in the breast image based on the acquired breast image, the estimated adipose image, the acquired pixel value of the directly irradiated region, and further, the stored predetermined value indicating the ratio of the average attenuation coefficients.

3. The mammary gland content rate estimating apparatus according to claim 2,
    wherein the mammary gland content rate calculating device calculates a mammary gland content rate G(x, y) of each of pixels in coordinates (x, y) of the breast image by the following expression:

$$G(x, y) = \frac{A(x, y) - I(x, y)}{I_0 - A(x, y)} \times \frac{1}{\mu - 1} \qquad \text{[Expression 1]}$$

where a pixel value in the coordinates (x, y) in the acquired breast image is set as I(x, y), a pixel value in coordinates (x, y) of the estimated adipose image is set as A(x, y), the acquired pixel value of the directly irradiated region is set as $I_0$, and the stored predetermined value indicating the ratio of the average attenuation coefficients is set as μ.

4. The mammary gland content rate estimating apparatus according to claim 3, further comprising
    a mammary gland volume ratio calculating device which calculates a volume ratio of the mammary glands by calculating a weighted average of the mammary gland content rates G(x, y) using ($I_0$–A(x, y)) of [Expression 1] as a weight.

5. The mammary gland content rate estimating apparatus according to claim 1,
    wherein the predetermined value indicating the ratio of the average attenuation coefficients of the mammary glands and the adipose is a fixed value which indicates a ratio of an average attenuation coefficient of mammary glands and an average attenuation coefficient of adipose when an average breast is imaged under average imaging conditions by the mammography imaging apparatus.

6. The mammary gland content rate estimating apparatus according to claim 1,
    wherein the predetermined value indicating the ratio of the average attenuation coefficients of the mammary glands and the adipose is about 1.778.

7. The mammary gland content rate estimating apparatus according to claim 1,
    wherein the adipose image estimating device includes:
    a skin line extracting device which extracts a skin line showing a boundary between a breast region and the directly irradiated region based on the acquired breast image; and
    an adipose image creating device which creates the adipose image by setting a pixel value of a pixel at an equal distance from the skin line at a pixel value determined in accordance with the distance from the skin line, based on an assumption that a thickness of a breast which is imaged is determined in accordance with a distance in a normal direction from the skin line.

8. The mammary gland content rate estimating apparatus according to claim 7,
    wherein the adipose image creating device comprises:
    a device which calculates a representative value representing adipose tissue from the pixel value of the pixel at the equal distance from the skin line based on the acquired breast image, for respective distances from the skin line; and
    a device which estimates a relational expression between the distance from the skin line and the pixel value of the adipose image based on the calculated representative value, wherein
    the pixel value of the adipose image corresponding to the distance from the skin line is determined based on the estimated relational expression.

9. A mammary gland content rate estimating method, comprising the steps of:

acquiring a breast image obtained by radiographing a breast by a mammography imaging apparatus;

estimating an adipose image from the acquired breast image based on an assumption that an entire breast is composed of only adipose tissues;

acquiring a pixel value of a directly irradiated region from the acquired breast image; and calculating a mammary gland content rate for each of pixels of the breast image based on the acquired breast image, the estimated adipose image and the acquired pixel value of the directly irradiated region.

10. The mammary gland content rate estimating method according to claim 9, further comprising the step of:

storing, in a storage device, a predetermined value indicating a ratio of average attenuation coefficients of mammary glands and adipose, in advance, wherein in the step of calculating the mammary gland content rate, the mammary gland content rate is calculated for each of the pixels in the breast image based on the acquired breast image, the estimated adipose image, the acquired pixel value of the directly irradiated region, and further, the predetermined value indicating the ratio of the average attenuation coefficients.

11. The mammary gland content rate estimating method according to claim 10, wherein in the step of calculating a mammary gland content rate, a mammary gland content rate $G(x, y)$ of each of pixels in coordinates $(x, y)$ of the breast image is calculated by the following expression:

$$G(x, y) = \frac{A(x, y) - I(x, y)}{I_0 - A(x, y)} \times \frac{1}{\mu - 1} \quad \text{[Expression 1]}$$

where a pixel value in the coordinates $(x, y)$ in the acquired breast image is set as $I(x, y)$, a pixel value in coordinates $(x, y)$ of the estimated adipose image is set as $A(x, y)$, the acquired pixel value of the directly irradiated region is set as $I_0$, and the stored predetermined value expressing the ratio of the average attenuation coefficients is set as $\mu$.

12. The mammary gland content rate estimating method according to claim 11, further comprising the step of calculating a weighted average of the mammary gland content rates $G(x, y)$ using $(I_0 - A(x, y))$ of [Expression 1] as a weight to obtain a volume ratio of the mammary glands.

13. A recording medium on which a program is recorded, the program comprising computer-executable instructions of:

acquiring a breast image obtained by radiographing a breast by a mammography imaging apparatus;

estimating an adipose image from the acquired breast image based on an assumption that an entire breast is composed of only adipose tissues;

acquiring a pixel value of a directly irradiated region from the acquired breast image; and calculating a mammary gland content rate for each of pixels of the breast image based on the acquired breast image, the estimated adipose image and the acquired pixel value of the directly irradiated region.

* * * * *